(12) United States Patent
Mann et al.

(10) Patent No.: US 12,146,177 B2
(45) Date of Patent: Nov. 19, 2024

(54) METHODS OF MAKING AND USING E,Z,E-GERANYLGERANYL DIPHOSPHATE

(71) Applicant: WiSys Technology Foundation, Inc., Madison, WI (US)

(72) Inventors: Francis Michelle Mann, Oak Creek, WI (US); Leah C. Poulos, Kenosha, WI (US)

(73) Assignee: WiSys Technology Foundation, Inc., Madison, WI (US)

( * ) Notice: Subject to any disclaimer, the term of this patent is extended or adjusted under 35 U.S.C. 154(b) by 244 days.

(21) Appl. No.: 17/197,941

(22) Filed: Mar. 10, 2021

(65) Prior Publication Data

US 2021/0285016 A1 Sep. 16, 2021

Related U.S. Application Data

(60) Provisional application No. 62/987,496, filed on Mar. 10, 2020.

(51) Int. Cl.
| | |
|---|---|
| *C12P 5/00* | (2006.01) |
| *A61K 9/00* | (2006.01) |
| *C12N 9/02* | (2006.01) |

(52) U.S. Cl.
CPC ............ *C12P 5/007* (2013.01); *A61K 9/0014* (2013.01); *C12N 9/0073* (2013.01); *C12Y 505/01013* (2013.01)

(58) Field of Classification Search
None
See application file for complete search history.

(56) References Cited

U.S. PATENT DOCUMENTS

2002/0004218 A1* 1/2002 Rodan .................... A61K 31/00 435/21

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Mohan et al. Archives of Biochemistry and Biophysics (1996), 330(1), 33-47. Abstract. (Year: 1996).*
Accession P9WFF4. Apr. 16, 2014 (Year: 2014).*
Accession O06428. Jul. 1, 1997 (Year: 1997).*
Accession O50410. Jun. 1, 1998 (Year: 1998).*

Cina, Nicholas, "Computation Modeling of GGPP Synthase Proteins Found in *Mycobacterium tuberculosis* and Their Possible Bactericidal Effects (Thesis)", University of Wisconsin-Parkside, (May 16, 2019), 25 pgs.
Dhiman, Rakesh, et al., "Identification of a novel class of w, E, E-farnesyl diphosphate synthase from *Mycobacterium tuberculosis*", Journal of Lipid Research, vol. 45, (2004), 18 pgs.
Ferrari, Lara, "E, Z, E-GGPP, a Novel Bactericidal Compound (Thesis)", University of Wisconsin-Parkside, (Dec. 14, 2020), 25 pgs.
Kaur, Devinder, et al., "Decaprenyl Diphosphate Synthesis in *Mycobacterium tuberculosis*", Journal of Bacteriology, vol. 186, No. 22, (2004), 7564-7570.
Liu, Chia-L, et al., "A Cholesterol Biosynthesis Inhibitor Blocks *Staphylococcus aureus* Virulence", Science, 319(5868), (2008), 9 pgs.
Mann, Francis, et al., "Functional characterization and evolution of the isotuberculosinol operon in *Mycobacterium tuberculosis* and related Mycobacteria", Frontiers in Microbiology, vol. 3, Article 368, (2012), 8 pgs.
Mann, Francis, et al., "Rv0989c encodes a novel (E)-geranyl diphosphate synthase facilitating decaprenyl diphosphate biosynthesis in *Mycobacterium tuberculosis*", FEBS Letters, 585, (2011), 549-554.
Nagel, Raimund, "Arginine in the FARM and SARM: A Role in Chain-Length Determination for Arginine in the Aspartate-Rich Motifs of Isoprenyl Diphosphate Synthases from *Mycobacterium tuberculosis*", Molecules, 23(10), (2018), 7 pgs.
Nygaard, Courtney, et al., "(Poster) Identification of Alternative Pathways to Prenyl Diphosphates Involved in Cell Wall Assembly in *Mycobacterium tuberculosis*", Department of Chemistry, Winona State University, (Sep. 1, 2012), 1 pg.
Poulos, Leah, "(E, Z, E)-GGPP: A Novel Potential Bactericidal Isoprenoid from *Mycobacterium tuberculosis* (thesis)", University of Wisconsin-Parkside, (May 16, 2020), 30 pgs.
Schulbach, Mark, et al., "Identification of a Short (C15) Chain Z-Isoprenyl Diphosphate Synthase and a Homologous Long (C50) Chain Isoprenyl Diphosphate Synthase in *Mycobacterium tuberculosis*", The Journal of Biological Chemistry, vol. 275, No. 30, (2000), 22876-22881.
Zahn, Todd J, et al., "Synthesis and Evaluation of GGPP Geometric Isomers Divergent Substrate Specificities of FTase and GGTase I", Bioorganic and Medicinal Chemistry Letters 11, (2001), pp. 1605-1608.

* cited by examiner

*Primary Examiner* — Christian L Fronda
(74) *Attorney, Agent, or Firm* — Schwegman Lundberg & Woessner, P.A.

(57) ABSTRACT

Methods of making and using E,Z,E-GGPP are provided. Also provided are expression cassettes encoding isoprenyl diphosphate synthases, e.g., cis- or trans-isoprenyl diphosphate synthases.

9 Claims, 8 Drawing Sheets

Figure 1:
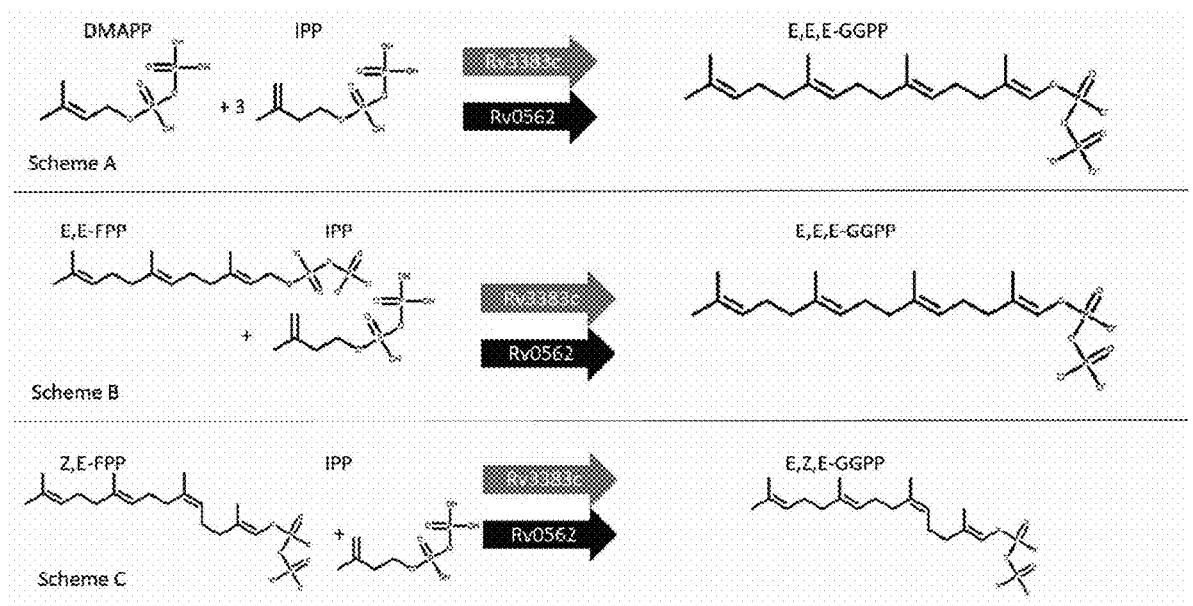
Figure 2:
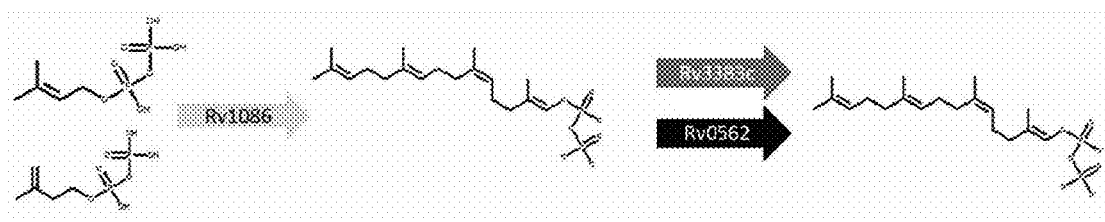
Figure 3:
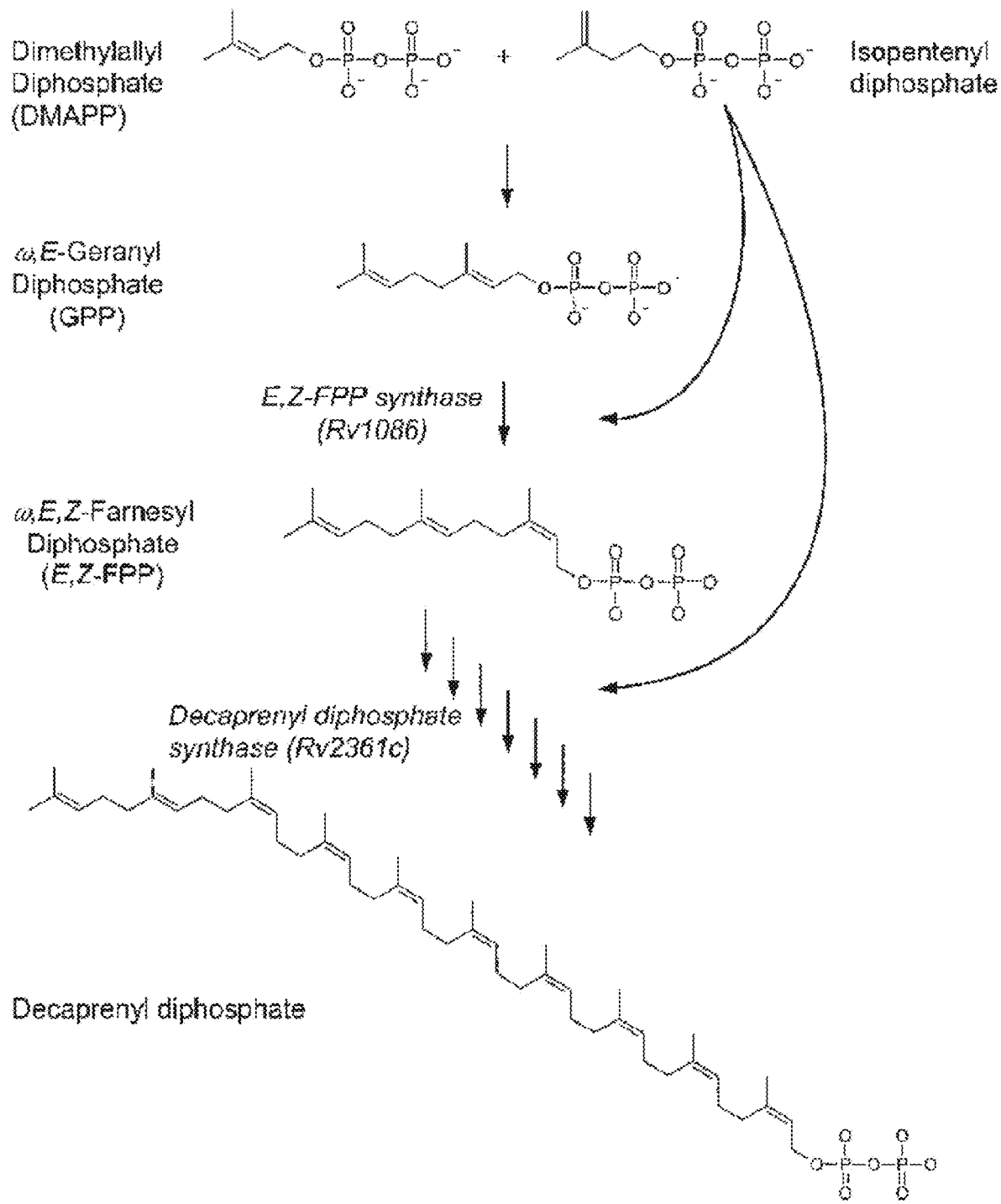

Specification includes a Sequence Listing.

| Name | Description | Modifiers |
|---|---|---|
| Negative control | IPP/DMAPP no enz | Keep in water bath overnight |
| Positive control | 10 µM GGPP no enz | Keep in water bath for 30 minutes |
| Rv1086 control | IPP/DMAPP + Rv1086 | Keep in water bath for 30 minutes |
| Rv0562/Rv3383c control | IPP/EEFPP + Rv0562/3383c | Keep in water bath for 30 minutes |
| Rv0562/Rv3383c + ZEFPP | IPP/ZEFPP + Rv0562/3383c | Keep in water bath for 30 minutes |
| Rv0562/Rv3383c + ZEFPP | IPP/ZEFPP + Rv0562/3383c | Keep in water bath overnight |
| Experiment 1 | IPP/DMAPP + Rv1086 + Rv0562/3383c | 20 µL clarified lysate, keep in water bath for 30 minutes |
| Experiment 2 | IPP/DMAPP + Rv1086 + Rv0562/3383c | 300 µg Rv1086 and either GGPP synthase, keep in water bath for 30 minutes |
| Experiment 3 | IPP/DMAPP + Rv1086 + Rv0562/3383c | 100 µL Rv1086 and either GGPP synthase, keep in water bath for 30 minutes |
| Experiment 4 | IPP/DMAPP + Rv1086 + Rv0562/3383c | 100 µL Rv1086 and either GGPP synthase, keep in water bath overnight |
| Experiment 5 | IPP/DMAPP + Rv1086, wait then add Rv0562/3383c | 300 µg each enzyme; allow Rv1086, IPP/DMAPP to incubate for ten minutes then add GGPP synthase |
| Experiment 6 | Rv1086 + Rv0562/3383c, wait then add IPP/DMAPP | 100µL each enzyme; allow Rv1086 and either GGPP synthase to incubate for ten minutes then add IPP/DMAPP |

FIG. 4

Rv1086

VEIIPPRLKEPLYRLYELRLRQGLAASKSDLPRHIAVLCDGNRRWARSAGYDDVSYGYRM
GAAKIAEMLRWCHEAGIELATVYLLSTENLQRDPDELAALIEIITDVVEEICAPANHWSV
RTVGDLGLIGEEPARRLRGAVESTPEVASFHVNVAVGYGGRREIVDAVRALLSKELANGA
TAEELVDAVTVEGISENLYTSGQPDPDLVIRTSGEQRLSGFLLWQSAYSEMWFTEAHWPA
FRHVDFLRALRDYSARHRSYGR    (SEQ ID NO:10)

MEIIPPRLKEPLYRLYELRLRQGLAASKSDLPRHIAVLCDGNRRWARSAGYDDVSYGYRM
GAAKIAEMLRWCHEAGIELATVYLLSTENLQRDPDELAALIEIITDVVEEICAPANHWSV
RTVGDLGLIGEEPARRLRGAVESTPEVASFHVNVAVGYGGRREIVDAVRALLSKELANGA
TAEELVDAVTVEGISENLYTSGQPDPDLVIRTSGEQRLSGFLLWQSAYSEMWFTEAHWPA
FRHVDFLRALRDYSARHRSYGR (SEQ ID NO:1)

Rv3383c

MGGVLTLDAAFLGSVPADLGKALLERARADCGPVLHRAIESMREPLATMAGYHLGWWNAD
RSTAAGSSGKYFRAALVYAAAAACGGDVGDATPVSAAVELVHNFTLLHDDVMDGDATRRG
RPTVWSVWGVGVAILLGDALHATAVRILTGLTDECVAVRAIRRLQMSCLDLCIGQFEDCL
LEGQPEVTVDDYLRMAAGKTAALTGCCCALGALVANADDATIAALERFGHELGLAFQCVD
DLIGIWGDPGVTGKPVGNDLARRKATLPVVAALNSRSEAATELAALYQAPAAMTASDVER
ATALVKVAGGGHVAQRCADERIQAAIAALPDAVRSPDLIALSQLICRREC (SEQ ID NO:3)

Rv0562

VRTPATVVAGVDLGDAVFAAAVRAGVARVEQLMDTELRQADEVMSDSLLHLFNAGGKRFR
PLFTVLSAQIGPQPDAAAVTVAGAVIEMIHLATLYHDDVMDEAQVRRGAPSANAQWGNNV
AILAGDYLLATASRLVARLGPEAVRIIADTFAQLVTGQMRETRGTSENVDSIEQYLKVVQ
EKTGSLIGAAGRLGGMFSGATDEQVERLSRLGGVVGTAFQIADDIIDIDSESDESGKLPG
TDVREGVHTLPMLYALRESGPDCARLRALLNGPVDDDAEVREALTLLRASPGMARAKDVL
AQYAAQARHELALLPDVPGRRALAALVDYTVSRHG (SEQ ID NO:11)

MRTPATVVAGVDLGDAVFAAAVRAGVARVEQLMDTELRQADEVMSDSLLHLFNAGGKRFR
PLFTVLSAQIGPQPDAAAVTVAGAVIEMIHLATLYHDDVMDEAQVRRGAPSANAQWGNNV
AILAGDYLLATASRLVARLGPEAVRIIADTFAQLVTGQMRETRGTSENVDSIEQYLKVVQ
EKTGSLIGAAGRLGGMFSGATDEQVERLSRLGGVVGTAFQIADDIIDIDSESDESGKLPG
TDVREGVHTLPMLYALRESGPDCARLRALLNGPVDDDAEVREALTLLRASPGMARAKDVL
AQYAAQARHELALLPDVPGRRALAALVDYTVSRHG (SEQ ID NO:2)

FIG. 6

METHODS OF MAKING AND USING E,Z,E-GERANYLGERANYL DIPHOSPHATE

CROSS-REFERENCE TO RELATED APPLICATIONS

This application claims the benefit of the filing date of U.S. application No. 62/987,496, filed on Mar. 10, 2020, the disclosure of which is incorporated by reference herein.

BACKGROUND

The genome of *Mycobacterium tuberculosis* (Mtb) encodes many enzymes involved in isoprenoid synthesis and exhibits considerable plasticity in the metabolism. Isoprenyl diphosphate synthases (IDSs) are enzymes that catalyze the polymerization of terpenoid precursors isopentenyl diphosphate (IPP) with allylic isoprenoids, such as dimethylallyl diphosphate (DMAPP), geranyl diphosphate (GPP), and farnesyl diphosphate (FPP). The stereochemistry of the product is determined by the enzyme utilized, and mixed stereochemistry products are generated by stepwise elongation and transfer to active sites. Mtb encodes five trans-IDSs and two cis-IDSs, many of which are co-expressed in the host at the same time.

SUMMARY

During characterization of alternate products by recombining specific Mtb isoprenoid synthases in a heterologous host, e.g., *Escherichia coli*, recombination of a cis-IDS (e.g., Rv1086, SEQ ID NO:1; SEQ ID NO:10 is mutated for expression in *E. coli*) with one of two trans-IDSs capable of producing longer products, e.g., (Rv0562 or Rv3383c; SEQ ID NO:2 and SEQ ID NO: 11, and SEQ ID NO:3, respectively), resulted in significant cell death. The product of both of these combinations is likely E,Z,E-GGPP, which is a form of GGPP that has not been observed in nature. In addition, purification and combination of the enzymes outside of a host cell resulted in a product that bears the appropriate molecular mass and chromatographic shift to putatively identify it as E,Z,E-GGPP, indicating production of E,Z,E-GGPP is correlated to cell death of *E. coli*. E,Z,E-GGPP may be produced by the coexpression of both Rv1086 and one GGPP synthase. E,Z,E-GGPP is thus a bactericidal agent and may serve as an appropriate prodrug or topical antibacterial agent. Specifically, it was demonstrated that recombination of a Z,E-FPP synthase (e.g., Rv1086) with at least two E,E,E-GGPP synthases from *Mycobacterium tuberculosis* (e.g., Rv3383c and Rv0562 in a vector within the heterologous host *Escherichia coli* resulted in cell death or a significant reduction in viability of the host, whereas neither individual expression of any individual synthase nor combinations of other *M. tuberculosis* derived isoprenoid synthases tested (e.g., Rv0989c+Rv1086, Rv0989c+Rv3383c, Rv0989c+Rv0562, Rv0989c+Rv1086+Rv2361c, Rv3398c+Rv3383c, Rv3398c+Rv0562, and Rv3398c+Rv0526+Rv2361c) resulted in a similar phenotype. In addition, E,Z,E-GGPP was observed in enzyme co-assays of Z,E-FPP synthase (Rv1086) in conjunction with either GGPP-synthase, Rv0562 or Rv3383c and in enzyme assays including either GGPP-synthase, Rv0562 or Rv3383c, in combination with synthetic Z,E-FPP.

In one embodiment, the disclosure provides for a product produced by combining a cis-isoprenyl diphosphate synthase, at least one trans-isoprenyl diphosphate synthase, and a substrate(s) therefore, e.g., an isoprenoid and an allylic isoprenoid. In one embodiment, a cis-isoprenyl diphosphate synthase, trans-isoprenyl diphosphate synthase, and isoprenoid precursor, e.g., isopentenyl pyrophosphate (IPP), and an allylic isoprenoid, e.g., DMAPP, GPP or FPP, are in a cell. In one embodiment, a cis-isoprenyl diphosphate synthase, trans-isoprenyl diphosphate synthase, and at least two substrates therefor, e.g., isopentenyl pyrophosphate (IPP) and an allylic substrate, are in a cell-free reaction.

The disclosure also provides for a host cell expressing at least one heterologous isoprenyl diphosphate synthase. In one embodiment, the host cell is a prokaryotic cell, e.g., *E. coli*. In one embodiment, the heterologous isoprenyl diphosphate synthase is a prokaryotic isoprenyl diphosphate synthase. In one embodiment, the isoprenyl diphosphate synthase is a *Mycobacterium* isoprenyl diphosphate synthase. In one embodiment, the heterologous isoprenyl diphosphate synthases catalyzes a reaction with IPP, e.g., IPP or IPP and DMAPP or FPP.

Further provided is a method to produce an isoprenoid. In one embodiment, one or more isolated isoprenyl diphosphate synthases, e.g., in the presence of substrate(s), are combined, concurrently or sequentially, in an amount to produce a product, e.g., E,Z,E-GGPP. In one embodiment, the method includes combining an isolated cis-isoprenyl diphosphate synthase, a trans-isoprenyl diphosphate synthase, and a substrate(s) therefor. The product of the method may be employed to, for example, disinfect a surface, e.g., the epidermis of a vertebrate. In one embodiment, the polymer comprises DMAPP, FPP or GPP. Thus, the product is useful to prevent, inhibit or treat a microbial infection in a vertebrate. In one embodiment, the vertebrate is a mammal. In one embodiment, the vertebrate is a human. In one embodiment, the product is locally administered to a vertebrate. In one embodiment, the product is systemically administered to a vertebrate. In one embodiment, the product is injected into the vertebrate. In one embodiment, the product is orally administered to the vertebrate.

Pharmaceutical compositions comprising E,Z,E-GGPP or a derivative thereof, e.g., produced via chemical syntheses or enzymatic reactions are also provided. In one embodiment, the derivative is E,Z,E-geranylgeranyl methyl bisphosphonate, E,Z,E-geranylgeranyl bisphosphonate, E,Z,E-geranylgeraniol, E,Z,E-geranylgeranyl chloride, or E,Z,E-geranylgeranyl tosylate

BRIEF DESCRIPTION OF FIGURES

FIG. 1. Exemplary products of Rv3383c and Rv0562. Scheme A: Naturally, both Rv0562 and Rv3383c condense 3 IPP and one DMAPP to produce E,E,E-GGPP. Scheme B: Naturally, both Rv0562 and Rv3383c condense 3 IPP and one E,E-FPP to produce E,E,E-GGPP. Scheme C: Potentially, synthetic Z,E-FPP could be elongated by Rv0562 or Rv3383c to produce E,Z,E-GGPP.

FIG. 2. Exemplary biosynthetic pathway for E,Z,E-GGPP in a heterologous host. Coexpression of Rv1086 and either Rv0562 or Rv3383c results in loss of cell viability in heterologous host *E. coli*.

FIG. 3. Biosynthetic pathway of decaprenyl diphosphate.

FIG. 4. Details for Example 3.

FIGS. 5A-5C. Purified protein shown by 1-D SDS PAGE. On all gels, lanes 1-8 are the Protein Ladder (Fisher BioReagentsEZ-Run Protein Marker (A, B) Fisher BioReagentsEZ-Run PrestainedProtein Marker (C)), Clarified Lysate, Pellet, Decant, Wash 1, Wash 2, Wash 3 and Eluant, respectively. (A) The gel of Rv1086/17 has a distinct band at its monomeric molecular weight of 29,410 Da. (B) The gel of Rv0562/17 has a distinct band at its monomeric molecular weight of 35,528 Da. (C) The gel of Rv3383c has a distinct band at its molecular weight of 36,432 Da.

FIG. 6. Representative sequences of enzymes useful in the synthesis of E,Z,E-GGPP (SEQ ID Nos. 1-3 and 10-11).

FIG. 7. Exemplary products of Rv3383c and Rv0562.

Figure 8:
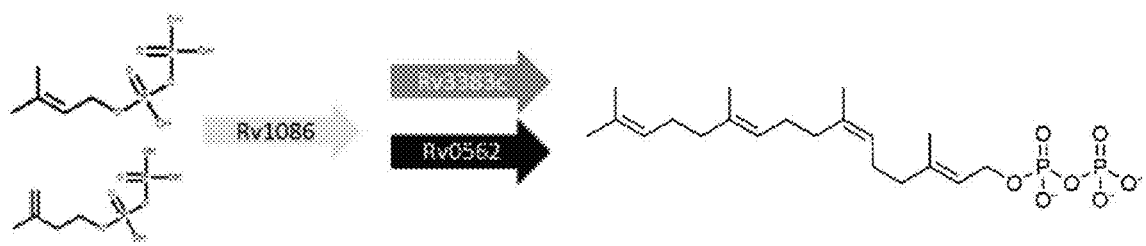

FIG. 8. Exemplary biosynthetic pathway for E,Z,E-GGPP in a heterologous host.

Figure 9A:
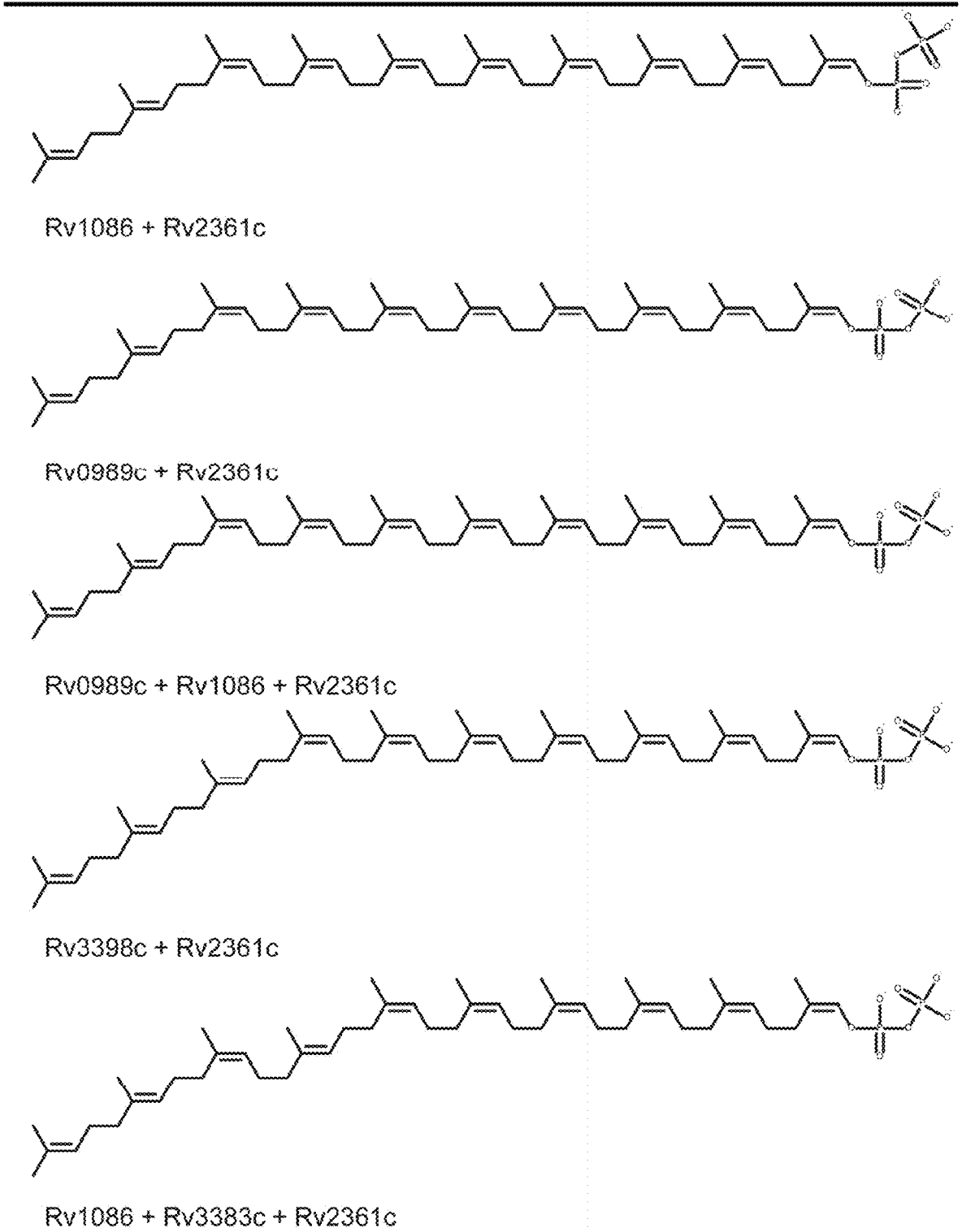
Figure 9B:
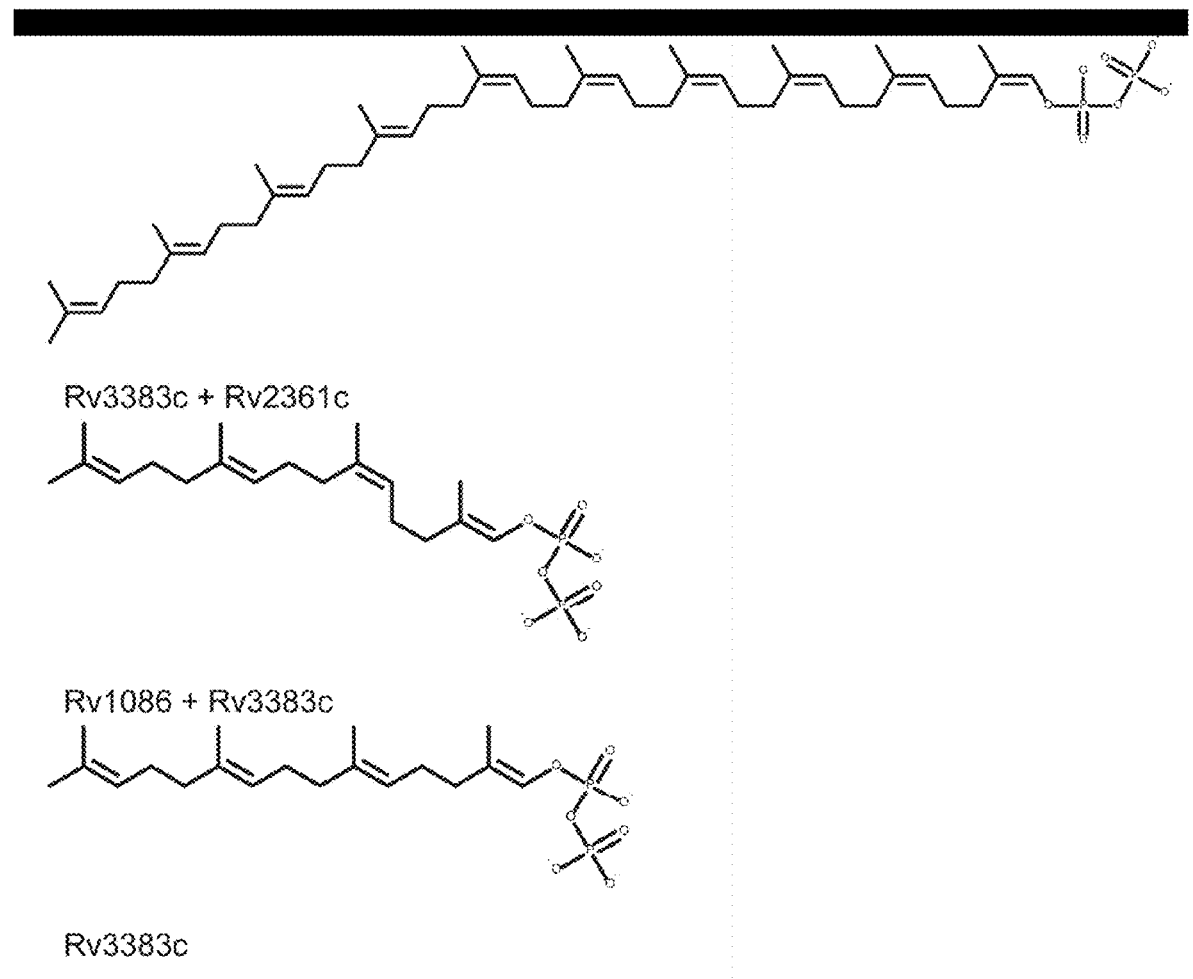

FIGS. 9A-9B. Exemplary structures produced by various enzymes.

DETAILED DESCRIPTION

Terpenoids are a large class of organic natural products derived from activated isoprenoid units, isopentenyl pyrophosphate (IPP) and dimethylallyl pyrophosphate (DMAPP), used in all domains of life. Both *Escherichia coli* (*E. coli*) and *Mycobacterium tuberculosis* (Mtb) utilize isoprenoid glycosyl carriers for cell wall and membrane biosynthesis but their carriers differ slightly. *E. coli* utilizes undecaprenyl diphosphate (UPP), composed of 11 stereospecific isoprene units, while Mtb utilizes decaprenyl diphosphate (DPP), composed of 10 stereospecific isoprene units. Three main enzymes are employed by Mtb to synthesize DPP:

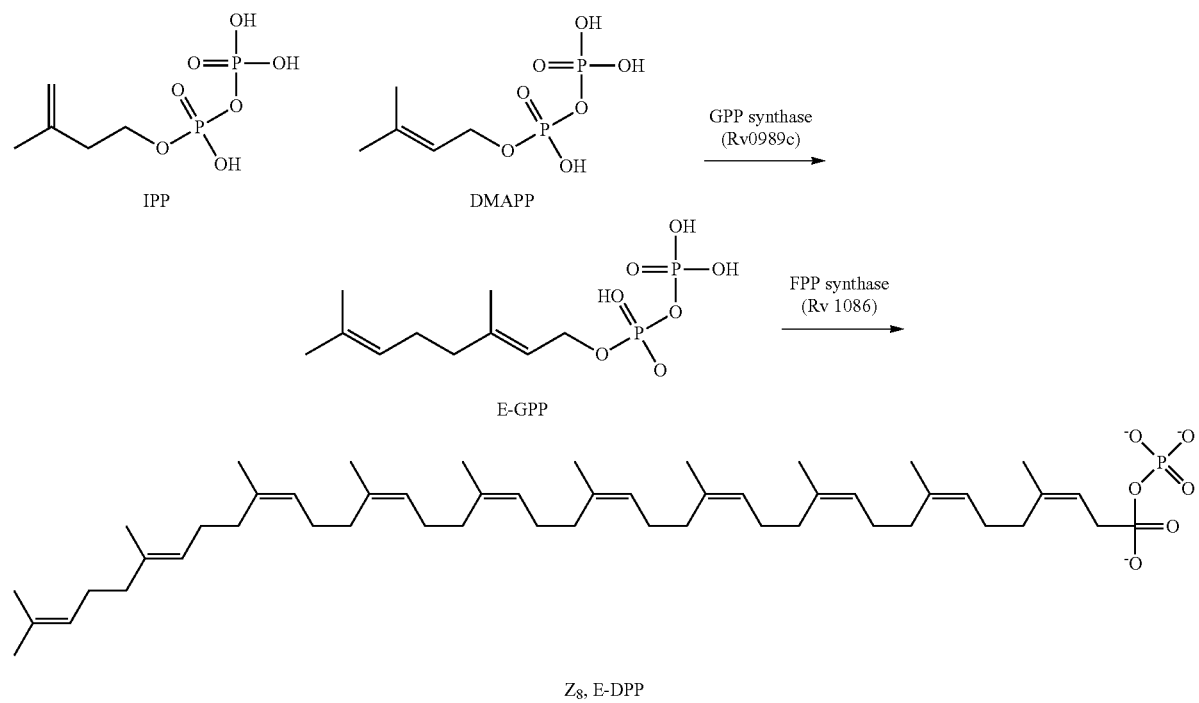

Beyond synthesizing DPP, Mtb has been shown to have a flexible terpenoid metabolism and undergoes alternate pathways resulting in different products. Elongation of E,E-FPP once by GGPP synthase (Rv3383c or Rv0562) results in E,E,E-GGPP. However, as described in more detail below, Rv1086 in conjunction with either GGPP synthase resulted in a novel product that is putatively E,Z,E-GGPP, a terpenoid with stereochemistry unobserved before in nature.

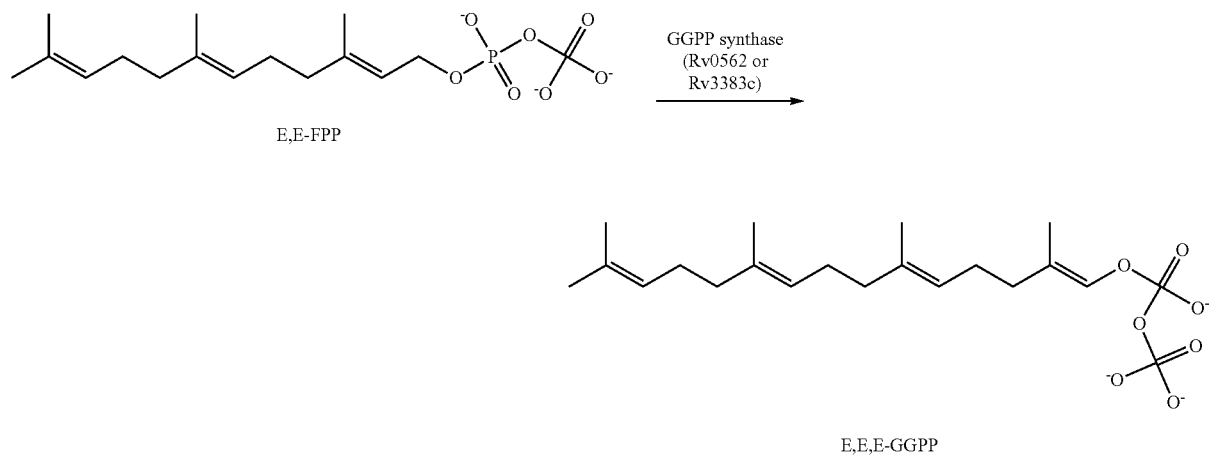

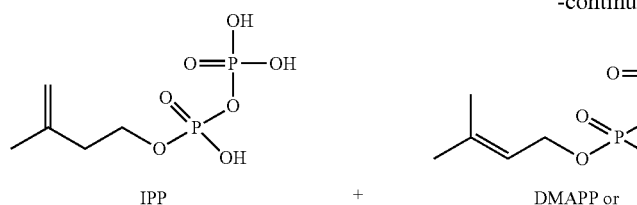

-continued

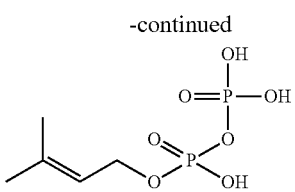

IPP + DMAPP or Z,E-FPP

E,E-FPP

E,Z,E-GGPP

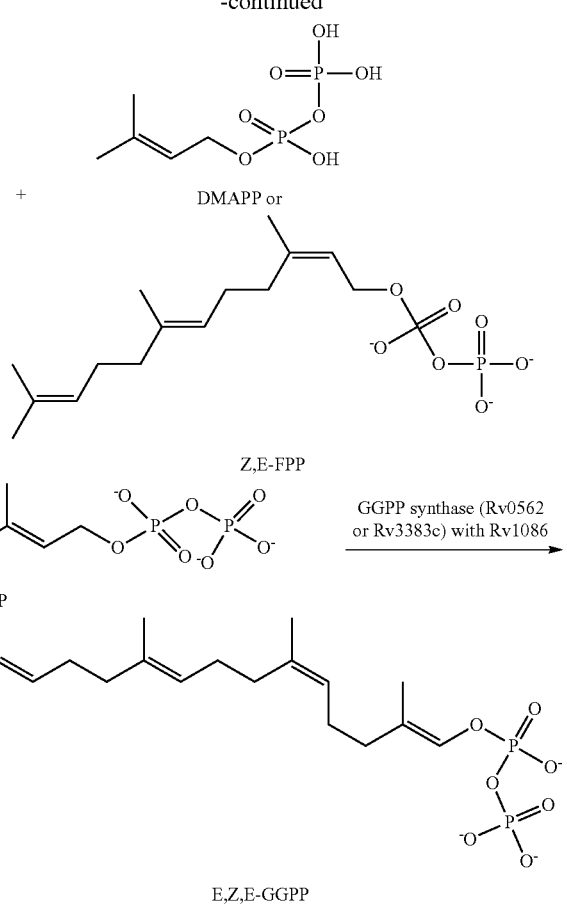

Terpenoids are commonly used by organisms in the kingdom Bacteria for cell wall and membrane biosynthesis, electron transportation, and conversion of light into chemical energy. *Mycobacterium tuberculosis* (Mtb) utilizes terpenoid glycosyl carriers to assemble extracellular matrices. Mtb uses three main enzymes to produce $Z_8$,E-decaprenyl diphosphate ($Z_8$,E-DPP): two isoprene units are polymerized to produce E-geranyl diphosphate (Rv0989c), which is elongated by Z-FPP synthase (Rv1086) to produce Z,E-Farnesyl diphosphate (Z,E-FPP) which is elongated to $Z_8$,E-DPP by DPP synthase (Rv2361c). It has been previously demonstrated that DPPS is able to utilize different substrates like GPP, NPP, E,E-FPP and E,E,E-GGPP, many of which are available in the Mtb metabolome. However, metabolite profiling of Mtb has failed to demonstrate significant amounts of any alternate glycocarriers.

In an attempt to produce alternate forms of DPP using *E. coli* as a heterologous host, it was noted that combinations of Mtb isoprenoid synthases, e.g., Rv1086 combined with either of the encoded E,E,E-GGPP synthases (Rv0562 or Rv3383c), resulted in complete death of the host. Further investigation using affinity chromatography to purify the enzymes individually and assess product formation via coupled assay resulted in a very small amount of a product. This product is likely an isomer of GGPP, as determined by mass spectral analysis and chromatographic separation, and supports the hypothesis that an alternate terpenoid product that is bactericidal for *E. coli* can be generated by Mtb metabolism.

Computational modeling was performed to assess the potential for *M. tuberculosis* enzymes to accept a Z-FPP substrate. It was observed that the unique width of the active sites of Rv0562 and Rv3383c protein products could harbor such a product. Other GGPP synthases, such as those produced by *Corynebacterium glulamicum*, are unlikely to produce the product. The gene encoding the enzyme from *C. glutamicum* is cloned to confirm that hypothesis.

Assuming the product acts as an inhibitor of a crucial enzyme or process in the host, several targets were identified that may be inhibited by an unusual stereochemistry of GGPP. *Escherichia coli* may be inhibited in the production of undecaprenyl diphosphate, menaquinone, or various prenylated proteins. A more general toxicity by membrane disruption is also possible.

Antibiotic resistance is a growing problem, with multiple bacteria exhibiting complete or near-complete resistance to all known antibiotics. Disruption of cell wall and/or lipopolysaccharide production and the electron transport chain are both well-characterized mechanisms by which antibiotics function. Novel antibiotic scaffolds are one of medicine's greatest needs as bacteria continue their race to evolve antibiotic resistance. As disclosed herein, a specific combination of enzymes from the bacterium *Mycobacterium tuberculosis* can cause cell death in the heterologous host *Escherichia coli* (*E. coli*). In vitro studies determined that a novel compound that is putatively (E,Z,E)-GGPP is generated by these enzymes. As this compound appears to be a bactericidal agent for *Escherichia coli*, it could function as a bactericidal agent for other bacteria. Additionally, similar compounds, such as farnesyl methyl bisphosphonate have demonstrated selective inhibition of terpenoid biosynthetic pathways in bacteria and mammals. This compound could act as molecule for similar applications.

Definitions

An "isolated" polynucleotide, e.g., plasmid, polypeptide or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Isolated nucleic acid, peptide or polypeptide is present in a form or setting that is different from that in which it is found in nature.

The terms "polypeptide" and "protein" are used interchangeably herein to refer to polymers of amino acids of any length. The terms also encompass an amino acid polymer that has been modified; for example, disulfide bond formation, glycosylation, acetylation, phosphorylation, lipidation, or conjugation with a labeling component.

The term "exogenous," when used in relation to a protein, gene, nucleic acid, or polynucleotide in a cell or organism refers to a protein, gene, nucleic acid, or polynucleotide which has been introduced into the cell or organism by artificial or natural means. An exogenous nucleic acid may be from a different organism or cell, or it may be one or more additional copies of a nucleic acid which occurs naturally within the organism or cell. By way of a non-limiting example, an exogenous nucleic acid is in a chromosomal location different from that of natural cells, or is otherwise flanked by a different nucleic acid sequence than that found in nature, e.g., an expression cassette which links a promoter from one gene to an open reading frame for a gene product from a different gene.

"Transformed" or "transgenic" is used herein to include any host cell or cell line, which has been altered or augmented by the presence of at least one recombinant DNA sequence. The host cells are typically produced by transfection with a DNA sequence in a plasmid expression vector, as an isolated linear DNA sequence, or infection with a recombinant viral vector.

The term "polynucleotide" refers to a polymeric form of nucleotides of any length, including deoxyribonucleotides or ribonucleotides, or analogs thereof. A polynucleotide may comprise modified nucleotides, such as methylated or capped nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

"Heterologous" means derived from a genotypically distinct entity from the entity to which it is compared. For example, a polynucleotide introduced by genetic engineering techniques into a different cell type is a heterologous polynucleotide (and, when expressed, can encode a heterologous polypeptide). Similarly, a transcriptional regulatory element such as a promoter that is removed from its native coding sequence and operably linked to a different coding sequence is a heterologous transcriptional regulatory element.

As used herein, "pharmaceutically acceptable salts" refer to derivatives of the disclosed compounds where the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, behenic, salicylic, sulfanilic, 2-acetoxybenzoic, fumaric, toluenesulfonic, methanesulfonic, ethane disulfonic, oxalic, isethionic, and the like.

The pharmaceutically acceptable salts of the compounds described herein can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile may be employed. Lists of suitable salts are found in *Remington's Pharmaceutical Sciences*, 17th ed., Mack Publishing Company, Easton, Pa., p. 1418 (1985), the disclosure of which is hereby incorporated by reference.

The compounds described herein can be solvates, and in some embodiments, hydrates. The term "solvate" refers to a solid compound that has one or more solvent molecules associated with its solid structure. Solvates can form when a compound is crystallized from a solvent. A solvate forms when one or more solvent molecules become an integral part of the solid crystalline matrix upon solidification. The compounds of the formulas described herein can be solvates, for example, ethanol solvates. Another type of a solvate is a hydrate. A "hydrate" likewise refers to a solid compound that has one or more water molecules intimately associated with its solid or crystalline structure at the molecular level. Hydrates can form when a compound is solidified or crystallized in water, where one or more water molecules become an integral part of the solid crystalline matrix.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The following definitions are used, unless otherwise described: halo or halogen is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Het can be heteroaryl, which encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

Some compounds may exhibit polymorphism. It is to be understood that any racemic, optically-active, polymorphic, or stereoisomeric form, or mixtures thereof, of a compound described herein, which possess the useful properties described herein, It is also understood by those of skill in the art that the compounds described herein include their various tautomers, which can exist in various states of equilibrium with each other.

The terms "treat" and "treating" as used herein refer to (i) preventing a pathologic condition from occurring (e.g., prophylaxis); (ii) inhibiting the pathologic condition or arresting its development; (iii) relieving the pathologic condition; and/or (iv) ameliorating, alleviating, lessening, and removing one or more symptoms of a condition. A candidate molecule or compound described herein may be in an amount in a formulation or medicament, which is an amount that can lead to a biological effect, or lead to protection from, ameliorating, alleviating, lessening, relieving, diminishing or a disease condition, e.g., infection, for example. These terms also are applicable to reducing a titer of a microorganism (microbe) or infectious agent in a system (e.g., cell, tissue, or subject) infected with a microbe, reducing the rate of microbial propagation, reducing the duration of infection of an infectious agent, delaying or attenuating an infection by an infectious agent, reducing the number of symptoms or an effect of a symptom associated with the microbial infection, and/or removing detectable amounts of the microbe from the system. Examples of symptoms include but are not limited weight loss, fever, malaise, weakness, dehydration, failure or diminished organ or organ system function (e.g., pulmonary function). Examples of microbes include but are not limited to viruses, bacteria and fungi.

The term "therapeutically effective amount" as used herein refers to an amount of a compound, or an amount of a combination of compounds, to treat or prevent a disease or disorder or a microbial infection, or to treat or prevent a symptom of the disease or disorder or microbial infection, in a subject. As used herein, the terms "subject" and "patient" generally refers to an individual who will receive or who has received treatment (e.g., administration of a compound) according to a method described herein.

"Stable compound" and "stable structure" are meant to indicate a compound that is sufficiently robust to survive isolation to a useful degree of purity from a reaction mixture, and formulation into an efficacious therapeutic agent. Only stable compounds are contemplated.

As used herein, the term "salts" includes "pharmaceutically acceptable salts" as well as other salts. "Salts" refers to derivatives of the disclosed compounds wherein the parent compound is modified by making acid or base salts thereof. Examples of salts include alkali salts and alkali earth salts of an ionized form of the disclosed compounds. For example, a lithium salt, sodium salt, potassium salt, calcium salt, or magnesium salt. The disclosed compounds may be a salt comprising a cationic metal and an anionic organic compound, for example, a compound having an oxyanion and a sodium cation. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric (or larger) amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

Useful dosages can be determined by comparing their in vitro activity, and in vivo activity in models. Methods for the extrapolation of effective dosages in mice, and other animals, to humans are known to the art; for example, see U.S. Pat. No. 4,938,949. The pharmaceutical compositions and compounds described herein can generally be administered in the form of a dosage unit (e.g. tablet, capsule, etc.) in an amount from, for example, about 1 ng/kg of body weight to about 0.5 g/kg of body weight, or from about 1 µ/kg of body weight to about 500 mg/kg of body weight, or from about 10 µ/kg of body weight to about 250 mg/kg of body weight, for example, from about 20 µ/kg of body weight to about 100 mg/kg of body weight. Those skilled in the art will recognize that the particular quantity of pharmaceutical composition and/or compounds described herein administered to an individual will depend upon a number of factors including the biological effect desired and the condition of the subject.

Exemplary Formulations

In one embodiment, the formulation comprises particles comprising the one or more compounds described herein. The disclosed particles, e.g., biodegradable microparticles, may include or may be formed from biodegradable polymeric molecules which may include, but are not limited to polylactic acid (PLA), polyglycolic acid (PGA), co-polymers of PLA and PGA (i.e., polyactic-co-glycolic acid (PLGA)), poly-ε-caprolactone (PCL), polyethylene glycol (PEG), poly(3-hydroxybutyrate), poly(p-dioxanone), polypropylene fumarate, poly(orthoesters), polyol/diketene acetals addition polymers, poly-alkyl-cyano-acrylates (PAC), poly(sebacic anhydride) (PSA), poly(carboxybiscarboxyphenoxyphenoxy hexone (PCPP) poly[bis (p-carboxypheonoxy)methane](PCPM), copolymers of PSA, PCPP and PCPM, poly(amino acids), poly(pseudo amino acids), polyphosphazenes, derivatives of poly[(dichloro) phosphazenes] and poly[(organo)phosphazenes], poly-hydroxybutyric acid, or S-caproic acid, elastin, or gelatin. (See, e.g., Kumari et al., Colloids and Surfaces B: Biointerfaces 75 (2010) 1-18; and U.S. Pat. Nos. 6,913,767; 6,884,435; 6,565,777; 6,534,092; 6,528,087; 6,379,704; 6,309,569; 6,264,987; 6,210,707; 6,090,925; 6,022,564; 5,981,719; 5,871,747; 5,723,269; 5,603,960; and 5,578,709; and U.S. Published Application No. 2007/0081972; and International Application Publication Nos. WO 2012/115806; and WO 2012/054425; the contents of which are incorporated herein by reference in their entireties).

The disclosed particles may be prepared by methods known in the art. (See, e.g., Nagavarma et al., Asian J. of Pharma. And Clin. Res., Vol 5, Suppl 3, 2012, pages 16-23; Cismaru et al., Rev. Roum. Chim., 2010, 55(8), 433-442; and International Application Publication Nos. WO 2012/115806; and WO 2012/054425; the contents of which are incorporated herein by reference in their entireties). Suitable methods for preparing particles may include methods that utilize a dispersion of a preformed polymer, which may include but are not limited to solvent evaporation, nanoprecipitation, emulsification/solvent diffusion, salting out, dialysis, and supercritical fluid technology. In some embodiments, the particles may be prepared by forming a double emulsion (e.g., water-in-oil-in-water) and subsequently performing solvent-evaporation. The particles may be subjected to further processing steps such as washing and lyophilization, as desired. Optionally, the particles may be combined with a preservative (e.g., trehalose).

In one embodiment, the particles have a mean effective diameter of less than 500 microns, e.g., the particles have a mean effective diameter of between about 1 μm and about 500 μm, e.g., between about 5 μm and about 25 μm, about 10 μm and about 20 μm, about 15 μm and about 25 μm, about 100 μm to about 150 μm, or about 45 μm to 650 μm. In one embodiment, the particles have a mean effective diameter of less than 50 microns, e.g., the particles have a mean effective diameter of between about 0.01 μm and about 50 μm, e.g., between about 0.5 μm and about 5 μm, about 1 μm and about 10 μm, about 1 μm and about 7.5 μm, about 5 μm to about 10 μm, or about 2 μm to about 5 μm. The size of the particles (e.g., mean effective diameter) may be assessed by known methods in the art, which may include but are not limited to transmission electron microscopy (TEM), scanning electron microscopy (SEM), Atomic Force Microscopy (AFM), Photon Correlation Spectroscopy (PCS), Nanoparticle Surface Area Monitor (NSAM), Condensation Particle Counter (CPC), Differential Mobility Analyzer (DMA), Scanning Mobility Particle Sizer (SMPS), Nanoparticle Tracking Analysis (NTA), X-Ray Diffraction (XRD), Aerosol Time of Flight Mass Spectroscopy (ATFMS), and Aerosol Particle Mass Analyzer (APM).

In one embodiment, a particles comprise polymers including but not limited to poly(lactic-co-glycolic acid) (PLGA), polylactic acid (PLA), linear and/or branched PEI with differing molecular weights (e.g., 2, 22 and 25 kDa), dendrimers such as polyamidoamine (PAMAM) and polymethoacrylates; lipids including but not limited to liposomes, emulsions, DOTAP, DOTMA, DMRIE, DOSPA, distearoylphosphatidylcholine (DSPC), DOPE, or DC-cholesterol; peptide based vectors including but not limited to poly-L-lysine or protamine; or poly(β-amino ester), chitosan, PEI-polyethylene glycol, PEI-mannose-dextrose, DOTAP-cholesterol or RNAiMAX.

In one embodiment, the particle is a glycopolymer-based particle, poly(glycoamidoamine)s (PGAAs). These materials are created by polymerizing the methylester or lactone derivatives of various carbohydrates (D-glucarate (D), meso-galactarate (G), D-mannarate (M), and L-tartarate (T)) with a series of oligoethyleneamine monomers (containing between 1-4 ethylenamines (Liu and Reineke, 2006). A subset composed of these carbohydrates and four ethyleneamines in the polymer repeat units may yield exceptional delivery efficiency.

In one embodiment, the particles comprise polyethyleneimine (PEI), polyamidoamine (PAMAM), PEI-PEG, PEI-PEG-mannose, dextran-PEI, OVA conjugate, PLGA microparticles, or PLGA microparticles coated with PAMAM, or any combination thereof. The polymer may include, but is not limited to, polyamidoamine (PAMAM) dendrimers. Polyamidoamine dendrimers suitable for preparing the particles may include 3rd-, 4th-, 5th-, or at least 6th-generation dendrimers.

In one embodiment, the delivery vehicle may be particles or liposomes comprising a cationic lipid, e.g., N-[1-(2,3-dioleoyloxy)propel]-N,N,N-trimethylammonium (DOTMA), 2,3-dioleyloxy-N-[2-spermine carboxamide] ethyl-N,N-dimethyl-1-propanammonium trifluoracetate (DOSPA, Lipofectamine); 1,2-dioleoyl-3-trimethylammonium-propane (DOTAP); N-[1-(2,3-dimyristioxy) propyl]; N,N-dimethyl-N-(2-hydroxyethyl) ammonium bromide (DMRIE), 3-β-[N—(N,N-dimethylaminoethane) carbamoyl] cholesterol (DC-Chol); dioctadecyl amidoglyceryl spermine (DOGS, Transfectam); or imethyldioctadeclyammonium bromide (DDAB). The positively charged hydrophilic head group of cationic lipids usually consists of monoamine such as tertiary and quaternary amines, polyamine, amidinium, or guanidinium group. A series of pyridinium lipids have been developed (Zhu et al., 2008; van der Woude et al., 1997; Ilies et al., 2004). In addition to pyridinium cationic lipids, other types of heterocyclic head group include imidazole, piperizine and amino acid. The main function of cationic head groups is to condense negatively charged molecules by means of electrostatic interaction to slightly positively charged particles, leading to enhanced cellular uptake and endosomal escape.

Lipids having two linear fatty acid chains, such as DOTMA, DOTAP and SAINT-2, or DODAC, may be employed as a delivery vehicle, as well as tetraalkyl lipid chain surfactant, the dimer of N,N-dioleyl-N,N-dimethylammonium chloride (DODAC). All the trans-orientated lipids regardless of their hydrophobic chain lengths ($C_{16:1}$, $C_{18:1}$ and $C_{20:1}$) appear to enhance the transfection efficiency compared with their cis-orientated counterparts.

The structures of polymers include but are not limited to linear polymers such as chitosan and linear poly(ethyleneimine), branched polymers such as branch poly(ethyleneimine) (PEI), circle-like polymers such as cyclodextrin, network (crosslinked) type polymers such as crosslinked poly(amino acid) (PAA), and dendrimers. Dendrimers consist of a central core molecule, from which several highly branched arms 'grow' to form a tree-like structure with a manner of symmetry or asymmetry. Examples of dendrimers include polyamidoamine (PAMAM) and polypropylenimine (PPI) dendrimers.

DOPE and cholesterol are commonly used neutral co-lipids for preparing liposomes. Branched PEI-cholesterol water-soluble lipopolymer conjugates self-assemble into cationic micelles. Pluronic (poloxamer), a non-ionic polymer and SP1017, which is the combination of Pluronics L61 and F127, may also be used.

In one embodiment, PLGA particles are employed to increase the encapsulation frequency although other materials, for example, PEI, DOTMA, DC-Chol, or CTAB, may be used.

In one embodiment, the particles comprise hydrogels of poloxamers, polyacrylamide, poly(2-hydroxyethyl methacrylate), carboxyvinyl-polymers (e.g., Carbopol 934, Goodrich Chemical Co.), cellulose derivatives, e.g., methylcellulose, cellulose acetate and hydroxypropyl cellulose, polyvinyl pyrrolidone or polyvinyl alcohols, or combinations thereof.

In some embodiments, a biocompatible polymeric material is derived from a biodegradable polymeric such as collagen, e.g., hydroxylated collagen, fibrin, polylactic-polyglycolic acid, or a polyanhydride. Other examples include, without limitation, any biocompatible polymer, whether hydrophilic, hydrophobic, or amphiphilic, such as ethylene vinyl acetate copolymer (EVA), polymethyl methacrylate, polyamides, polycarbonates, polyesters, polyethylene, polypropylenes, polystyrenes, polyvinyl chloride, polytetrafluoroethylene, N-isopropylacrylamide copolymers, poly(ethylene oxide)/poly(propylene oxide) block copolymers, poly(ethylene glycol)/poly(D,L-lactide-co-glycolide) block copolymers, polyglycolide, polylactides (PLLA or PDLA), poly(caprolactone) (PCL), or poly(dioxanone) (PPS).

In another embodiment, the biocompatible material includes polyethyleneterephalate, polytetrafluoroethylene, copolymer of polyethylene oxide and polypropylene oxide, a combination of polyglycolic acid and polyhydroxyalkanoate, gelatin, alginate, poly-3-hydroxybutyrate, poly-4-hydroxybutyrate, and polyhydroxyoctanoate, and polyacrylonitrilepolyvinylchlorides.

In one embodiment, the following polymers may be employed, e.g., natural polymers such as starch, chitin, glycosaminoglycans, e.g., hyaluronic acid, dermatan sulfate and chrondrotin sulfate, and microbial polyesters, e.g., hydroxyalkanoates such as hydroxyvalerate and hydroxybutyrate copolymers, and synthetic polymers, e.g., poly(orthoesters) and polyanhydrides, and including homo and copolymers of glycolide and lactides (e.g., poly(L-lactide, poly(L-lactide-co-D,L-lactide), poly(L-lactide-co-glycolide, polyglycolide and poly(D,L-lactide), pol(D,L-lactide-coglycolide), poly(lactic acid colysine) and polycaprolactone.

In one embodiment, the biocompatible material is derived from isolated extracellular matrix (ECM). ECM may be isolated from endothelial layers of various cell populations, tissues and/or organs, e.g., any organ or tissue source including the dermis of the skin, liver, alimentary, respiratory, intestinal, urinary or genital tracks of a warm blooded vertebrate. ECM may be from a combination of sources. Isolated ECM may be prepared as a sheet, in particulate form, gel form and the like.

The biocompatible polymer may comprise silk, elastin, chitin, chitosan, poly(d-hydroxy acid), poly(anhydrides), or poly(orthoesters). More particularly, the biocompatible polymer may be formed polyethylene glycol, poly(lactic acid), poly(glycolic acid), copolymers of lactic and glycolic acid, copolymers of lactic and glycolic acid with polyethylene glycol, poly(E-caprolactone), poly(3-hydroxybutyrate), poly(p-dioxanone), polypropylene fumarate, poly (orthoesters), polyol/diketene acetals addition polymers, poly(sebacic anhydride) (PSA), poly(carboxybiscarboxyphenoxyphenoxy hexone (PCPP) poly[bis (p-carboxypheonoxy) methane] (PCPM), copolymers of SA, CPP and CPM, poly(amino acids), poly(pseudo amino acids), polyphosphazenes, derivatives of poly[(dichloro)phosphazenes] or poly[(organo) phosphazenes], poly-hydroxybutyric acid, or S-caproic acid, polylactide-co-glycolide, polylactic acid, polyethylene glycol, cellulose, oxidized cellulose, alginate, gelatin or derivatives thereof.

Thus, the polymer may be formed of any of a wide range materials including polymers, including naturally occurring polymers, synthetic polymers, or a combination thereof. In one embodiment, the scaffold comprises biodegradable polymers. In one embodiment, a naturally occurring biodegradable polymer may be modified to provide for a synthetic biodegradable polymer derived from the naturally occurring polymer. In one embodiment, the polymer is a poly(lactic acid) ("PLA") or poly(lactic-co-glycolic acid) ("PLGA"). In one embodiment, the scaffold polymer includes but is not limited to alginate, chitosan, poly(2-hydroxyethylmethacrylate), xyloglucan, co-polymers of 2-methacryloyloxyethyl phosphorylcholine, poly(vinyl alcohol), silicone, hydrophobic polyesters and hydrophilic polyester, poly(lactide-co-glycolide), N-isoproylacrylamide copolymers, poly(ethylene oxide)/poly(propylene oxide), polylactic acid, poly (orthoesters), polyanhydrides, polyurethanes, copolymers of 2-hydroxyethylmethacrylate and sodium methacrylate, phosphorylcholine, cyclodextrins, polysulfone and polyvinylpyrrolidine, starch, poly-D,L-lactic acid-para-dioxanone-polyethylene glycol block copolymer, polypropylene, poly (ethylene terephthalate), poly(tetrafluoroethylene), poly-epsilon-caprolactone, or crosslinked chitosan hydrogels.

Subjects

The subject may be any animal, including a human and non-human animals. Non-human animals include all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses. The subject may also be livestock such as, cattle, swine, sheep, poultry, and horses, or pets, such as dogs and cats.

Subjects include human subjects suffering from or at risk for oxidative damage. The subject is generally diagnosed with the condition of the subject invention by skilled artisans, such as a medical practitioner.

The methods described herein can be employed for subjects of any species, gender, age, ethnic population, or genotype. Accordingly, the term subject includes males and females, and it includes elderly, elderly-to-adult transition age subjects adults, adult-to-pre-adult transition age subjects, and pre-adults, including adolescents, children, and infants.

Examples of human ethnic populations include Caucasians, Asians, Hispanics, Africans, African Americans, Native Americans, Semites, and Pacific Islanders. The methods of the invention may be more appropriate for some ethnic populations such as Caucasians, especially northern European populations, as well as Asian populations.

The term subject also includes subjects of any genotype or phenotype as long as they are in need of the invention, as described above. In addition, the subject can have the genotype or phenotype for any hair color, eye color, skin color or any combination thereof.

The term subject includes a subject of any body height, body weight, or any organ or body part size or shape.

EXEMPLARY EMBODIMENTS

The disclosure provides for a product produced by combining a cis-isoprenyl diphosphate synthase, e.g., one having at least 80%, 85%, 90%, 92%, 95%, 96%, 97%, 98% or 99% amino acid sequence identity to SEQ ID NO:1, at least one trans-isoprenyl diphosphate synthase, e.g., one having at least 80%, 85%, 90%, 92%, 95%, 96%, 97%, 98% or 99% amino acid sequence identity to SEQ ID NO:2 or SEQ ID NO:3, and substrates therefore, e.g., an isoprenoid and an allylic isoprenoid. In one embodiment, the product is E,Z,E-GGPP. In one embodiment, isolated E,Z,E-GGPP or a derivative thereof is provided.

In one embodiment, an isolated host cell expressing at least one heterologous isoprenyl diphosphate synthase is provided. In one embodiment, the host cell further expresses a second heterologous isoprenyl diphosphate synthase, wherein one of the synthases is a cis-isoprenyl diphosphate synthase and the other is a trans-isoprenyl diphosphate synthase. In one embodiment, the host cell is a prokaryotic cell. In one embodiment, the host cell is an Enterobacteriaceae. In one embodiment, the host cell is *E. coli*. In one embodiment, the heterologous isoprenyl diphosphate synthase is a *Mycobacterium* isoprenyl diphosphate synthase. In one embodiment, at least one heterologous isoprenyl diphosphate synthase catalyzes a reaction with GPP or FPP.

Further provided is a nucleic acid vector comprising a first expression cassette comprising a promoter operably linked to an open reading frame encoding a *Mycobacterium* isoprenyl diphosphate synthase. In one embodiment, the vector of is a plasmid. In one embodiment, the vector further comprises a second expression cassette comprising a promoter operably linked to an open reading frame encoding a different *Mycobacterium* isoprenyl diphosphate synthase. In one embodiment, the isoprenyl diphosphate synthase has at least 80%, 85%, 90%, 92%, 95%, 96%, 97%, 98% or 99% amino acid sequence identity to SEQ ID NO:1, SEQ ID NO:2 or SEQ ID NO:3.

Also provided is an in vitro method to produce a polymer comprising an allylic isoprenoid. The method includes culturing a host cell expressing at least two heterologous isoprenyl diphosphate synthases in an amount that provides for a polymer comprising an allylic isoprenoid, wherein one of the synthases is a cis-isoprenyl diphosphate synthase and the other is a trans-isoprenyl diphosphate synthase. In one embodiment, the isoprenyl diphosphate synthase has at least 80%, 85%, 90%, 92%, 95%, 96%, 97%, 98% or 99% amino acid sequence identity to SEQ ID NO:1, SEQ ID NO:2 or SEQ ID NO:3. In one embodiment, the host cell is a prokaryotic cell. In one embodiment, the host cell comprises an isoprenoid and an allylic isoprenoid. In one embodiment, the polymer comprises DMAPP, FPP or GPP.

In one embodiment, a method to disinfect a surface, is provided which includes applying to an surface a composition comprising an effective amount of E,Z,E-GGPP or a derivative thereof. In one embodiment, the surface is the skin of a vertebrate.

In one embodiment, a method to prevent, inhibit or treat a microbial infection in a vertebrate is provided. The method includes administering to the vertebrate a composition comprising an effective amount of E,Z,E-GGPP or a derivative thereof. In one embodiment, the vertebrate is a mammal. In one embodiment, the vertebrate is a human. In one embodiment, the administration is local, e.g., topical. In one embodiment, the administration is systemic. In one embodiment, the composition is injected. In one embodiment, the administration is oral.

Also provided is a composition comprising:

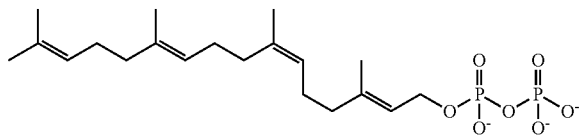 [SMILES: CC(C)=CCC/C(C)=C/CC/C(C)=C\CC/C(C)=C/COP(=O)([O-])OP(=O)([O-])[O-]]

In one embodiment, the composition further comprises a pharmaceutically acceptable carrier. In one embodiment, the composition is formulated for topical administration.

Routes of Administration

Administration of compositions described herein can be via any of suitable route of administration. One non-limiting example of a route of administration of a compound is to the skin.

Pulmonary administration can be used for delivery to the lungs and other regions of the respiratory system. Pulmonary administration includes, but is not limited to, aerosol inhalation via nasal (intranasal) or oral routes and intratracheal instillation. The respiratory system includes the nasal cavity and associated sinuses, the nasopharynx, oropharynx, larynx, trachea, bronchi, bronchioles, respiratory bronchioles, alveolar ducts and alveolar sacs. In specific embodiments the compounds described herein are administered to the lungs or the nasal cavity.

Aerosol inhalation is by any means by which an aerosol can be introduced into the respiratory system, including, but not limited to, pressurized metered dose inhalers, dry power inhalers and nebulisers (e.g., liquid spray and suspension spray) for oral route or any device suitable for intranasal administration.

In addition, in some embodiments, are provided various dosage formulations for inhalation delivery. For example, formulations may be designed for aerosol use in devices such as metered-dose inhalers, dry powder inhalers and nebulizers.

Intratracheal instillation can be carried out by delivering a solution into the lungs via a device, such as a syringe.

Intranasal administration which can be employed to effect pulmonary administration can be used specifically for administration to the nasal cavity and sinuses. Devises for intranasal administration include, but are not limited to liquid drop devices, spray devices, dry powder devices and aerosol devices. Intranasal administration can also be by nasal gel or insufflation.

Formulation of the compounds described herein as aerosols (solid or liquid particles), liquids, powders, gels, nanoparticles may be obtained using standard procedures well known in the art.

The compositions may also be administered parenterally, for example, intravenously, intra-arterially, intraperitoneally, intrathecally, intraventricularly, intraurethrally, intrasternally, intracranially, intramuscularly, or subcutaneously. Such administration may be as a single bolus injection, multiple injections, or as a short- or long-duration infusion. Implantable devices (e.g., implantable infusion pumps) may also be employed for the periodic parenteral delivery over time of equivalent or varying dosages of the particular formulation. For such parenteral administration, the compounds may be formulated as a sterile solution in water or another suitable solvent or mixture of solvents. The solution may contain other substances such as salts, sugars (particularly glucose or mannitol), to make the solution isotonic with blood, buffering agents such as acetic, citric, and/or phosphoric acids and their sodium salts, and preservatives.

The compositions can be formulated as pharmaceutical compositions and administered to a mammalian host, such as a human patient in a variety of forms adapted to the chosen route of administration, e.g., by pulmonary routes, orally or parenterally, by intravenous, intramuscular, topical or subcutaneous routes.

Thus, the present compositions may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compositions may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of adjuvants in such useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the adjuvants or other agents may be incorporated into sustained-release preparations and devices.

The compositions may also be administered intravenously or intraperitoneally by infusion or injection. Solutions of the compositions can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms during storage can be brought about by various antibacterial and antifungal agents, for example, parabens, chlorobutanol, phenol, sorbic acid, thimerosal, and the like. In many cases, it may be useful to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating compound(s) in the required amount in the appropriate solvent with various of the other ingredients enumerated above, as required, followed by filter sterilization. In the case of sterile powders for the preparation of sterile injectable solutions, one method of preparation includes vacuum drying and the freeze drying techniques, which yield a powder of the active ingredient plus any additional desired ingredient present in the previously sterile-filtered solutions.

For topical administration, the compounds may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages can be determined by comparing their in vitro activity, and in vivo activity in animal models. Methods for the extrapolation of effective dosages in mice, and other animals, to humans are known to the art; for example, see U.S. Pat. No. 4,938,949. The ability of a compound to act as a TLR agonist may be determined using pharmacological models which are well known to the art, including the procedures disclosed by Lee et al., *Proc. Natl. Acad. Sci. USA* 100: 6646 (2003).

Generally, the concentration of the active compound in a liquid composition, such as a lotion, will be from about 0.1-25 wt-%, e.g., from about 0.5-10 wt-%. The concentration in a semi-solid or solid composition such as a gel or a powder will be about 0.1-5 wt-%, e.g., about 0.5-2.5 wt-%.

The active ingredient may be administered to achieve peak plasma concentrations of the active compound of from about 0.5 to about 75 μM, e.g., about 1 to 50 μM, such as about 2 to about 30 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The amount of the active compound, or an active salt or derivative thereof, required for use in treatment will vary not only with the particular salt selected but also with the route of administration, the nature of the condition being treated and the age and condition of the patient and will be ultimately at the discretion of the attendant physician or clinician. In general, however, a suitable dose will be in the range of from about 0.5 to about 100 mg/kg, e.g., from about 10 to about 75 mg/kg of body weight per day, such as 3 to about 50 mg per kilogram body weight of the recipient per day, for instance in the range of 6 to 90 mg/kg/day, e.g., in the range of 15 to 60 mg/kg/day or in the range of from about 0.5 to about 100 mg/kg, e.g., from about 10 to about 75 mg/kg of body weight per day. More than one dose (e.g., 2, 3, 4, 5, 6, 7, 8, 9, 10, 11, 12, 13, 14, 15, 16, 17, 18, 19, 20, 21, 22, 23, 24, 25, 26, 27,or 28, or, for example, 35, 42, 49, 56, 63, or 70) may be determined by a physician or clinician to be required. Doses may be administered before, after, or before and after exposure to the infectious agent as determined by a physician or clinician based on the above discussed factors and other relevant factors. Scheduling of administration of doses (e.g., consecutive days, alternate days, multiple doses in one day) can also be determined by a physician or clinician based on the above discussed factors and other relevant factors.

The duration of treatment can be for a predetermined period of time. For example, 1, 2, 3, 4, 5, 6, 7 or more days, one week, two weeks, three weeks, four weeks or more. Alternatively, the duration of treatment can be for a period of time until the infectious agent is no longer detectable in the subject or the infectious agent is present at a level that does not result in symptoms or until there is an elimination or reduction in the number or severity of symptoms typically exhibited by a subject infected with a specific infectious agent. The duration of treatment can be determined by a physician or clinician based on the above discussed factors and other relevant factors.

The active compounds may be conveniently administered in unit dosage form; for example, containing 5 to 1000 mg, conveniently 10 to 750 mg, most conveniently, 50 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as by application of a plurality of drops into the eye. The dose, and perhaps the dose frequency, will also vary according to the age, body weight, condition, and response of the individual patient. In general, the total daily dose range for an active agent for the conditions described herein, may be from about 50 mg to about 5000 mg, in single or divided doses. In some embodiments, a daily dose range should be about 100 mg to about 4000 mg, e.g., about 1000-3000 mg, in single or divided doses, e.g., 750 mg every 6 hr of orally administered compound. This can achieve plasma levels of about 500-750 uM. In managing the patient, the therapy should be initiated at a lower dose and increased depending on the patient's global response.

In some embodiments the compound is not administered with a solvent or preservative such as DMSO or ethanol, which may have toxic effects, e.g., in humans.

Exemplary Methods

GGPP Synthase Assay

Assay buffer (10% glycerol, 50 mM HEPES, 1 mM DTT, 5 mM MgCl2·6 H2O, 10 mM KCl) was mixed with 100 μM IPP and an equivalent concertation of indicated stereochemical type of FPP, DMAPP or GPP. To each assay, 100 μL of purified enzyme was added then water was added to achieve a final volume of 1 mL. After the addition of the enzyme, the assays were conducted at 37° C. for 1 hour. After cooling, 3 U alkaline phosphatase was added according to the manufacturer protocol. The reaction was conducted overnight in the absence of light. The assays were next extracted thrice with 2 mL of GC-grade hexane. The hexane layers were then evaporated, and the organic samples were analyzed via GC equipped with an FID or MS detector.

Gas Chromatography

The samples were analyzed using a GC-2014 (Shimadzu) equipped with an FID detector alongside an AOC-20i auto injector. Using the auto injector, 5 μL of the samples were run through the 15 m column (SH-RxL-5 ms; 330° C. maximum temperature) with a flow rate of 5 mL/min. The temperature was initially set to 40° C. and allowed to raise to 300° C. over 20 minutes with one-minute run times and three-minute equilibrium intervals.

The invention will be further described by the following non-limiting examples.

Example 1

The key to one type of antibiotic resistance is thought to be the fastidious cell wall.

Mtb synthesizes a carrier composed of 10 stereospecific isoprene units that is produced by elongation of the two-unit (E)-GPP by the cis-FPP synthase, Rv1086, to produce (Z,E)-FPP which then has 35 carbons added in a cis-orientation by Rv2361c, resulting in (Z8,E)-decaprenyl diphosphate (DPP). Although this pathway is well characterized, multiple additional isoprenoid synthases are encoded in the Mtb genome, and previous in vitro studies indicated Rv2361c can utilize multiple alternate substrates. While attempting to understand the apparent flexibility of DPP metabolism, it was observed that heterologous co-expression of either of the encoded (E,E,E)-GGPP synthases, Rv0562 or Rv3383c, with Rv1086 in the heterologous host, *Escherichia coli* (*E. coli*), results in substantial cell death.

Computational modeling of both Rv0562 and Rv3383c suggest that both active sites may accept (Z,E)-FPP as a substrate, and if so, the product would be the novel compound (E,Z,E)-GGPP. Protein purifications of Rv0562 and Rv3383c individually combined with synthetic (Z,E)-FPP resulted in the synthesis of the terpenoid product, (E,Z,E)-GGPP. Subsequent in vitro coupled assays of Rv0562 or Rv3383c and Rv1086 resulted in higher product formation than those incubated with the synthetic substrate, supporting the production of the potentially bactericidal compound in E. coli.

All isoprenoids are synthesized by isoprenyl phosphate synthases (IPPS), which catalyze the chain elongation of allylic diphosphate substrates through head-to-tail condensation with IPP units. Elongation ends after reaching the desired chain length and substrates can be modified through dephosphorylation, cyclization, addition of a functional group and/or head-to-head condensation to produce the final product. IPPS are divided into two groups, cis and trans, defined by the stereochemistry of their product. Generally, cis-IPPS synthesize long-chain products (C30 or more) while trans-IPPS synthesize short-chain products (C20 or less).

The first enzyme of the pathway, encoded by Rv0989c (grcC2), is a trans-IPPS that catalyzes the head-to-tail condensation of IPP with DMAPP, its allylic substrate, to form geranyl diphosphate ((E)-GPP). The second enzyme, encoded by Rv1086., the first characterized short-chain cis-IPPS and only one in Mtb, has been deemed nonessential. It catalyzes the head-to-tail condensation of IPP with (E)-GPP, its preferred allylic substrate, to form farnesyl diphosphate ((Z,E)-FPP). It was also demonstrated that Rv1086 could condense IPP and neryl diphosphate (NPP), (E)-GPP's cis isomer, to form (Z,Z)-FPP. Rv1086 could produce small amounts of (Z,E)-FPP when incubated with DMAPP.

Experiments were designed to determine if either Mtb GGPP synthase (Rv0562 and/or Rv3383c) could utilize synthetic (Z,E)-FPP to make (E,Z,E)-GGPP and if either Mtb GGPP synthase (Rv0562 and/or Rv3383c) could utilize natural (Z,E)-FPP synthesized by Mtb's (Z,E)-FPP synthase (Rv1086), and to determine the mechanism by which coexpression of either Mtb GGPP synthase (Rv0562 or Rv3383c) and (Z,E)-FPP synthase (Rv1086) synthesized product.

The third enzyme, encoded by Rv2361c, was the other cis-IPPS in Mtb and it catalyzes the synthesis of DPP through seven successive condensations of IPP with (Z,E)-FPP as the first allylic substrate. Notably, Rv2361c demonstrates significant flexibility in allylic substrates; unlike other cis-IPPS, it is not specific for chain length or stereoconfiguration and will elongate (E)-GPP, NPP, (E,E)-FPP and geranylgeranyl diphosphate ((E,E,E)-GGPP) as well as its preferred substrate, (Z,E)-FPP.

Heterologous Expression of Rv0562, Rv3383c and Rv1086

Rv0562, Rv3383c and Rv1086 constructs from the H37Rv strain of Mtb were recombined into pDEST17 expression vectors to support the use of a 6×His N-terminal fusion tag. 2.0 µL of DNA was transformed into 20 µL of C41-DE3 E. coli cells, plated on NZY agar media (10 g/L NaCl, 10 g/L casein, 5.0 g/L yeast extract, 1.0 g/L MgSO4 (anhydrous), 1.5% agar, pH 7.0) with 0.1 M carbenicillin selection and incubated at 37° C. Colonies were inoculated into 5.0 mL starter cultures of NZY liquid media with 0.1 M carbenicillin selection and grown overnight at 37° C. under continuous shaking at 200 rpm. 1.5 mL of starter culture was inoculated into 1.0 L NZY media with 0.1 M carbenicillin selection and grown to an optical density at 600 nm (OD600) of 0.6 at 37° C. under continuous shaking at 200 rpm before being cooled to 20° C. and induced with 0.64 mM Isopropyl β-D-1-thiogalactopyranoside (IPTG), with subsequent 12-14 hour incubation at 18° C. under continuous shaking at 200 rpm.

Protein Purification

Cells were harvested via centrifugation and the resulting pellet was resuspended and homogenized in 10 mL lysis buffer (50 mM PO3 buffer, 150 mM NaCl, 10 mM MgCl2, 0.2 mM Phenylmethylsulfonylfluoride (PMSF, dissolved in isopropanol), pH 8.0). The homogenized suspension was lysed via three 10-second bursts of 30% amplitude sonication. The resulting lysates were then clarified via centrifugation (20 minutes×16,000 g, SA-600 rotor, 4° C.) and the resulting cell-free extracts were adhered to Ni-NTA Superflow resin (MilliporeSigma, Burlington, Mass., USA) and incubated at 4° C. for one hour on a nutating mixer. Excess buffer (hereby known as "decant") was removed from the adhered cell-free extracts via centrifugation (15 minutes× 2900 g, 4° C.). Crude recombinant proteins were washed thrice with lysis buffer via centrifugation (15 minutes×2900 g, 4 C) and eluted with elution buffer (150 mM imidazole, 50 mM PO3 buffer, 150 mM NaCl, 10 mM MgCl2, pH 8.0) to obtain purified proteins which were then immediately assayed for (E,Z,E)-GGPP synthase activity. 100 µL samples of lysate, clarified lysate, decant, washes and elutant were aliquoted off and set aside for later SDS-PAGE analysis to confirm the presence of pure protein.

SDS-PAGE

1-Dimensional SDS-PAGE was performed on all samples obtained from each protein purification. Gels were cast according to Bio-Rad's "Handcasting Polyacrylamide Gels" (4% Stacking Gel and 12% Resolving Gel) procedure or using Bio-Rad's TGX Stain-Free FastCast acrylamide kit, according to manufacturer protocol. An SDS-PAGE loading dye was prepared (62.5 mM Tris-HCl pH 6.8, 2.5% Sodium dodecyl sulfate (SDS), 0.002%, Bromophenol Blue, 0.7135M P-Mercaptoethanol). To prepare SDS-PAGE samples, 100 µL of lysate were diluted in 100 µL of lysis buffer and 100 µL of this dilution was added to 100 µL of loading dye. 100 µL of clarified lysate were diluted in 300 µL of lysis buffer and 100 µL of this dilution was added to 100 µL of loading dye. Approximately 100 µL solid volume of pellet was added to 100 µL of 9.0 M urea. The mixture underwent two cycles of vortexing and incubation at 42° C. in a water bath for 15 minutes and then 100 µL were diluted in 100 µL of lysis buffer. 100 µL of this dilution were added to 100 µL of loading dye. The decant, washes and eluant samples were not diluted with lysis buffer and instead put directly into loading dye. All samples in loading dye were incubated in a heat block at 100° C. for ten minutes. 10 µL of Protein Ladder (Fisher BioReagents EZ-Run Protein Marker or Fisher BioReagents EZ-Run Prestained Protein Marker) and each sample were pipetted into their corresponding lanes onto pre-cast gels. A 10×SDS Running buffer (30.3 g Tris base, 144.4 g Glycine, 10 g SDS, up to 1.0 L in dH2O) was prepared according to Cold Spring Harbor's protocol and a 1/10 dilution (1×) was used to run samples. Gels were allowed to run for 30-50 minutes at 500 V, 20 W and 200 mA. Then, gels were removed from casting plates and rinsed with deionized water prior to applying staining dye (50% Methanol, 0.1% Coomassie Brilliant Blue, 10% Glacial Acetic Acid). Gels were left to stain for thirty minutes and rotated every ten minutes before the stain was poured off. Gels were left in de-stain solution (50% Methanol, 40/6 dH2O, 10% Glacial Acetic Acid) overnight and stored in a 50:50 solution of de-stain and water at 4° C.

Coupled Assays

Protein concentrations were confirmed using spectrophotometric A280 values and the molar extinction coefficient determined by each protein's sequence. Protein sequences were obtained from Mycobrowser (mycobrowser.epfl.ch)

and entered into ExPASy's ProtParam tool (web.expasy.org/protparam/) to determine the molar extinction coefficients. Duplicates of all assay samples were made to ensure consistency of the data. Assays contained assay buffer (10% Glycerol, 100 mM HEPES, 100 mM KCl, 100 mM MgCl2·6 H2O), substrates (100 µM IPP and/or 100 µM DMAPP and/or 100 µM (E,E)/(Z,E)-FPP) and purified protein (Rv0562/Rv3383c and/or Rv1086. (Table 2) Total assay volume was 1.0 mL (molarities assume water). A negative control omitting substrates and three positive controls containing synthetic (E,E,E)-GGPP at 10 mM, 20 mM and 50 mM concentrations were made for standards. All standards were incubated in the water bath overnight at 37° C. to parallel the longest incubation period of experimental assays. Enzyme controls were made containing a single construct (Rv0562/Rv3383c/Rv1086) to confirm individual activities and GGPP synthases were incubated with synthetic (E,E)-FPP in the absence of Rv1086 to confirm autonomous elongation activity. The controls of Rv1086 with GPP and of Rv0562/Rv3383c with (E,E)-FPP and IPP were incubated in the water bath for 30 minutes at 37° C. To probe the first hypothesis, assays were made containing either GGPP synthase (Rv0562 or Rv3383c) and incubated with synthetic (Z,E)-FPP and IPP for two different lengths of time, 30 minutes and overnight, to see if product formation was possible. Eight experimental assays were developed to individually probe the conditions resulting in the production of (E,Z,E)-GGPP including analysis of the enzymatic activity of both GGPP synthase (Rv0562 and Rv3383c) when fed synthetic (Z,E)-FPP, the enzymatic activity of lysate, the enzymatic activity of clarified lysate, the effect of two different enzyme amounts (300 µg and 100 µL), the effect of two different incubation periods (30 minutes and overnight), the effect of pre-incubation of Rv1086 with Rv0562/Rv3383c and the effect of preincubation of Rv1086 and substrates (IPP/DMAPP) prior to addition of Rv0562/Rv3383c. Six of these assays were designed to probe the second hypothesis, that either GGPP synthase could utilize natural (Z,E)-FPP produced by Rv1086 to form the proposed product while assays including the preincubation of Rv1086 and either GGPP synthase were designed and performed to probe the third hypothesis, that synthesis of the novel product utilizing these two constructs in vivo occurs through heterodimer formation. Assays were stopped by the addition of 100 µL of CIP buffer (1.0 M Tris-HCl, 1.0 M MgCl2, 5.0 M NaCl, pH 9.5) and 3U 2.0 µL shrimp alkaline phosphatase, which dephosphorylates substrates and products, then incubated at either 25° C. overnight or 37° C. for 4 hours and protected from light to prevent photooxidation. Following incubation, assays were extracted thrice with 2.0 mL of GC-grade hexane, evaporated, resuspended in 100 µL of fresh hexanes and then stored in GC-MS autosampler vials at −20° C. prior to analysis by GC-FID and GC-MS.

Gas Chromatography—Flame Ionization Detection

Assays were analyzed using a Shimadzu GC2014 equipped with flame ionization detection (GC-FID) alongside an AOC-20i auto injector. Using the auto injector, 5.0 µL of each sample was injected at 250° C. to run through the 15 meter column (SH-Rxi-5 ms, 15×0.25×0.25) with a flow rate of 2.0 mL/minute. Assay analysis was performed following one of two protocols. For both, the initial column temperature was set to 40° C. and held for three minutes. The column was then raised either 20° C./minute until reaching 300° C., where it was held for four minutes, resulting in a total time of 20 minutes per assay ("fast" temperature gradient) or 15° C./minute until reaching 300° C., where it was held for three minutes resulting in a total time of 33 minutes per assay ("slow" temperature gradient). Products were confirmed by comparison to the retention time of dephosphorylated (E,E,E)-GGPP authentic standards.

Gas Chromatography—Mass Spectrometry

Assays were analyzed using a Shimadzu 2010Plus equipped with QP2010SE MS (GC-MS). 5.0 µL of each sample was injected at 100° C. to run through the 30 meter column (SH-Rxi-5Sil-MS, 30×0.25 ID×0.25 DF) with a flow rate of 5.0 mL/minute. Assay analysis was performed following the same "slow" temperature gradient described previously for the GC-FID. 1.2 kV ionization was applied between 5-17.5 minutes of the assay, scanning 50 m/z to 500 m/z.

Example 2

Terpenoids have been characterized and classified, each one is derived from the five carbon isoprene isomers isopentyl pyrophosphate (IPP) and dimethylallyl diphosphate (DMAPP). The condensation reactions that elongate these units by the method of head to tail polymerization are catalyzed by prenyltransferases proteins. Different types of prenyltransferases continue to polymerize and add IPP units to the chain.

Prenyltransferases are referred to as cis or trans depending the stereochemistry of their products. The decaprenyl diphosphate synthesis pathway in Mtb incorporates both cis and trans-prenyltransferases (Schulbach et al., 2000). The pathway is initiated by the trans-prenyltransferase enzyme Rv0989c which catalyzes the polymerization of IPP and DMAPP to make geranyl diphosphate (GPP). The resulting GPP can then be catalyzed by a variety of enzymes in pathways separate from decaprenyl diphosphate synthesis pathway to make geranylgeranyl pyrophosphate (GGPP) as well (Mann et al., 2012). Excluding these other pathways, GPP is a two-isoprene unit compound connected by a trans-bond and is an important precursor to the rest of decaprenyl diphosphate's synthesis. Next, a cis-prenyltransferase called Rv1086 adds another IPP unit to GPP to synthesize (Z,E)-FPP. Finally, decaprenyl diphosphate synthase sequentially adds seven more IPP units onto (Z,E)-FPP in the cis conformation to give decaprenyl diphosphate (Crick et al., 2001).

Rv1086 is unique to Mtb because it is the only short chain cis-polyprenyl transferase. Two trans-prenyltransferase enzymes in Mtb can bind and elongate (E,E)-FPP to synthesize (E,E,E)-GGPP. These GGPP synthase proteins are Rv0562 and Rv3383c. As disclosed herein, the co-expression of the cis-prenyltransferase Rv1086 with the trans-GGPP synthase enzymes Rv0562 or Rv3383c resulted in cell death within host *Escherichia coli* cells.

Methods

Unless otherwise stated, all chemicals were purchased from Fisher Scientific (St. Louis, Mo., USA). All molecular biology reagents were purchased from Invitrogen (Carlsbad, Calif., USA) and isoprenoids were purchased from Isoprenoids, LC (Tampa, Fla., USA).

Subcloning and Expression of Isoprenyl Diphosphates in *Escherichia coli*

All genes had been previously cloned, expressed with an N-terminal 6×His tag, purified, and characterized individually (Mann et al.). No toxicity was observed with expression of single constructs in *Escherichia coli* C41 (Lucigen, Middleton, Wis., USA).

Alternate constructs were produced using Gateway cloning technology (Invitrogen, Carlsbad, Calif., USA). Successful gene-vector recombinations can be found in Table 1. pACYC, and pCDF are DUET expression vectors (Novagen, Madison, Wis.) with one cloning site modified for Gateway expression using the Gateway Vector Conversion System (Thermo-Fisher). pDEST15 results in protein expression with an N-terminal fused Glutathione-S-transferase tag. pDEST17 results in protein expression with an N-terminal fused 6×His tag. Subcloning was completed in *Escherichia coli* Top10 cells (Invitrogen, Carlsbad, Calif., USA), which lack a T7 promoter recognition site, and thus do not result in protein synthesis.

TABLE 1

| Gene | pDEST15 | pDEST17 | pACYC-DEST | pCDF-DEST |
|---|---|---|---|---|
| Rv0562 | X | X | X | X |
| Rv1086 | X | X | | |
| Rv3383c | X | X | X | X |

X indicates successful subcloning.

Single construct transformations into C41 cells for protein expression were completed for each gene-vector combination and plated on NZY agar with appropriate concentrations of carbenicillin, chloramphenicol, and/or spectinomycin. Colonies were counted.

Double construct transformation into C41 cells for protein expression were completed for combinations with two different antibiotic resistance markers and plated on NZY agar containing the appropriate antibiotic combination. Colonies were counted.

Expression and Purification of Isoprenyl Diphosphate Synthases for Enzyme Assay

Genes (Rv0562, Rv3383c and Rv1086) recombined in pDEST17 expression vectors to enable use of an N-terminal 6×His tag were transformed into the C41 strain of *E. coli* (Lucigen, Middleton, Wis., USA) and plated on NZY agar with carbenicillin. Colonies were inoculated in 1 L NZY medium and grown to an optical density at 600 nm ($OD_{600}$) of 0.6 at 37° C. before being cooled to 20° C. and induced with 0.64 mM IPTG, with subsequent 12-14 hour incubation at 18° C. Cells were harvested via centrifugation and lysed in 10 mL lysis buffer (10 mM Tris-Cl, pH 6.8,) via sonication. The lysates were then clarified via centrifugation (20 minutes×16,000 g) and the resulting cell-free extracts were adhered to Ni-NTA Superflow resin (Novagen) with 2 mM PMSF, washed thrice with lysis buffer and eluted to purify enzyme. Samples of lysate, clarified lysate, washes and elutant were taken for SDS-PAGE to confirm the presence of pure protein.

Enzyme Assay

Purified enzymes were assayed in 50 mM sodium phosphate (pH 7.0), 10% glycerol, 10 mM MgCl2 with universal isoprenoid precursors isopentenyl diphosphate (IPP) and dimethylallyl diphosphate (DMAPP). Rv3383c and Rv0562 were also assayed in the presence of synthetic E,E-farnesyl diphosphate (EE-FPP) and Z,E-farnesyl diphosphate (ZE-FPP) in the presence of IPP. A variety of assay conditions were used to probe the conditions resulting in the production of E,Z,E-GGPP.

TABLE 2

| Construct 1 | Construct 2 | Colonies |
|---|---|---|
| Rv1086/15 | | 588 |
| Rv1086/17 | | 4200 |
| Rv3383c/CDF | | 1004 |

TABLE 2-continued

| Construct 1 | Construct 2 | Colonies |
|---|---|---|
| Rv0562/ACYC | | 6234 |
| Rv0562/CDF | | 695 |
| Rv3383c/CDF | Rv0562/ACYC | 1450 |
| Rv3383c/17 | Rv0562/ACYC | 2304 |
| Rv0562/17 | Rv3383c/CDF | 1856 |
| Rv1086/17 | Rv3383c/CDF | 0 |
| Rv1086/17 | Rv0562/ACYC | 17 |
| Rv1086/17 | Rv0562/CDF | 13 |
| Rv1086/15 | Rv3383c/CDF | 5 |
| Rv1086/15 | Rv0562/ACYC | 112 |
| Rv1086/15 | Rv0562/CDF | 41 |

Figure 5A:
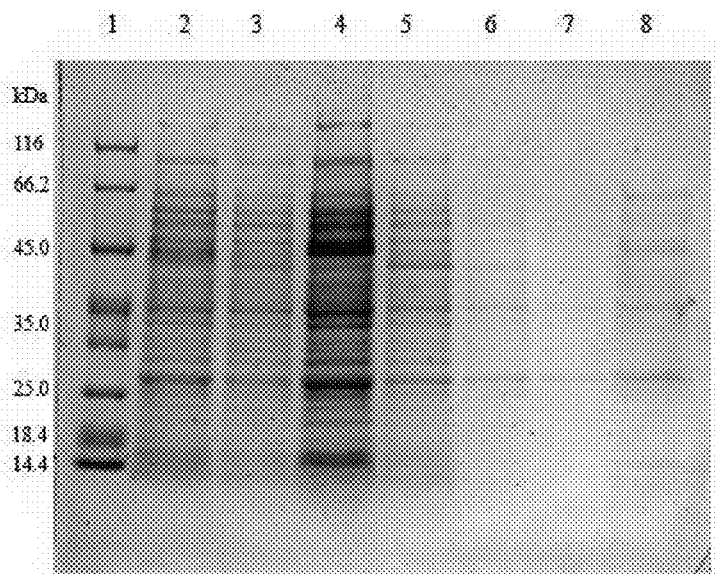
Figure 5B:
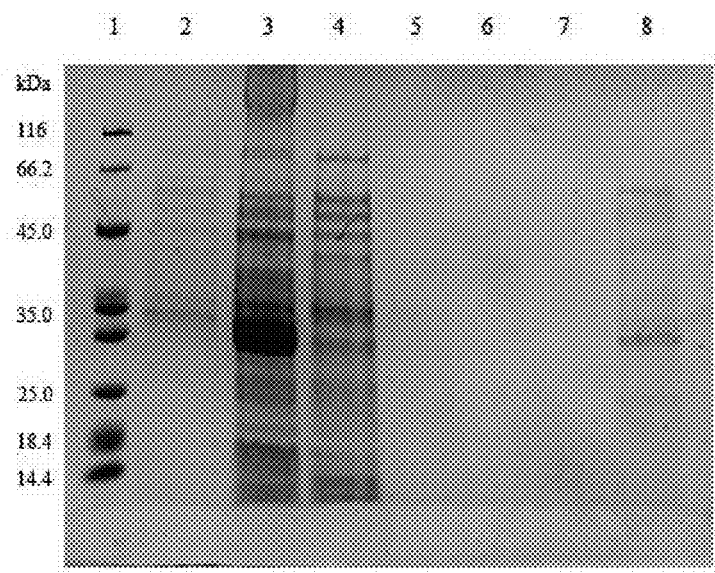
Figure 5C:
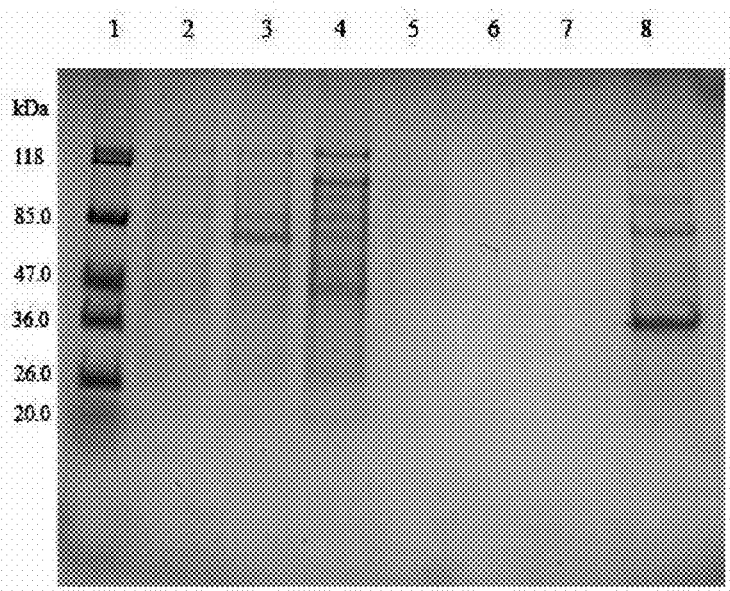
Figure 7:
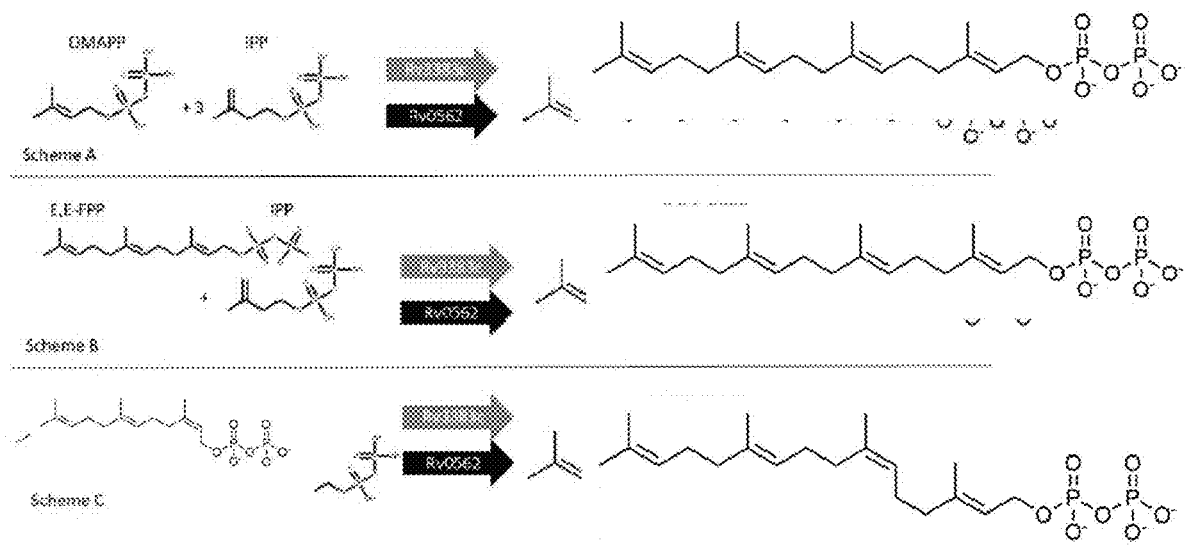

FIG. 5 shows purified protein on 1-D SDS PAGE. On all gels, lanes 1-8 are the protein ladder (Fisher BioReagent-sEZ-Run Protein Marker (A, B) Fisher BioReagentsEZ-Run PrestainedProtein Marker (C)), clarified lysate, pellet, decant, wash 1, wash 2, wash 3 and eluant, respectively. (A) The gel of Rv1086/17 has a distinct band at its molecular weight of 29,410 Da. This specific purification did not result in highly-pure protein, as shown by large quantities of protein present in the clarified lysate, decant and wash 1. (B) The gel of Rv0562/17 has a distinct band at its molecular weight of 35,528 Da. This specific purification did not result in large quantities of protein, as shown by the significant band in the Pellet band, indicating insoluble protein. (C) The gel of Rv3383c has a distinct band at its molecular weight of 36,432 Da. This purification was the most successful of the three, with the largest amount of soluble protein remaining in the eluant and minor amounts left behind in the clarified lysate or pellet.

Coexpression of Rv086 with either Rv3383c or Rv0562 resulted in significant reduction of cells, e.g., as a result of cell death. Cells expressing single plasmids resulted in high yields of colonies. Cells expressing combinations of Rv0562 and Rv3383c on differing plasmids also resulted in high yields of colonies (grey). Cells expressing Rv1086 and either Rv3383c or Rv0562 on an orthogonal plasmid resulted in colony counts that were less than 20% of lowest control yield (white).

Thus, recombination of Z,E-FPP synthase (Rv1086) with some E,E,E,-GGPP synthases from *Mycobacterium tuberculosis* (Rv3383c and Rv0562) within the heterologous host *E. coli* resulted in cell death or at least a significant reduction in viability of the host, whereas individual expression of any individual synthase or combination of any other two *M. tuberculosis* derived isoprenoid synthases resulted in a similar phenotype.

Example 3

Terpenoids, a large class of natural products, are commonly used by organisms in the kingdom Bacteria for cell wall and membrane biosynthesis, electron transportation, and conversion of light into chemical energy. *Mycobacterium tuberculosis* (Mtb) utilizes terpenoid glycosyl carriers to assemble extracellular matrices. Mtb uses three main enzymes to produce Z8,E-decaprenyl diphosphate (Z8,E-DPP): two isoprene units are polymerized to produce E-geranyl diphosphate (Rv0989c), which is elongated by Z-FPP synthase (Rv1086) to produce Z,E-Farnesyl diphosphate (Z,E-FPP) which is elongated to Z,E-DPP by DPP synthase (Rv2361c). It has been previously demonstrated that DPPS is able to utilize different substrates like GPP, NPP, E,E-FPP and, E,E,E-GGPP, many of which are available in the Mtb metabolome. However, metabolite profiling of Mtb has failed to demonstrate significant amounts of any alternate glycocarriers. In an attempt to produce alternate forms of DPP using *E. coli* as a heterologous host, it was noted that combinations of Mtb isoprenoid synthases, specifically Rv1086 combined with either of the encoded E,E,E-GGPP synthases (Rv0562 or Rv3383c), resulted in complete death of the host. Further investigation using affinity chromatography to purify the enzymes individually and assess product formation via coupled assay resulted in a very small amount of novel product. This product is likely an isomer of GGPP, as determined by mass spectral analysis and chromatographic separation, and supports the hypothesis that an alternate terpenoid product that is bactericidal for *E. coli* can be generated by Mtb metabolism.

Materials and Methods

Unless otherwise stated, all chemicals were purchased from Fisher Scientific (St. Louis, Mo., USA). All molecular biology reagents were purchased from Invitrogen (Carlsbad, Calif., USA) and isoprenoids were purchased from Isoprenoids, LC (Tampa, Fla., USA).

Heterologous expression of genes (Rv0562, Rv3383c and Rv1086) from the H37Rv strain of Mtb through recombination into pDEST17 expression vectors and transformation into the C41 strain of *E. coli* (Lucigen, Middleton, Wis., USA) was performed. Cells were induced with 0.64 mM IPTG and subsequently incubated at 18° C. for 12-14 hours.

DPP synthase (Rv2361c). DPPS is able to utilize different substrates like GPP, NPP, E,E-FPP and, E,E,E-GGPP, many of which are available in the Mtb metabolome. However, metabolite profiling of Mtb has failed to demonstrate significant amounts of any alternate glycocarriers. In an attempt to produce alternate forms of DPP using *E. coli* as a heterologous host, it was noted that combinations of Mtb isoprenoid synthases, specifically Rv1086 combined with either of the encoded E,E,E-GGPP synthases (Rv0562 or Rv3383c), resulted in complete death of the host.

Isoprenoids all derive from the polymerization of two simple precursors, each composed of a five-carbon chain: isopentenyl pyrophosphate (IPP) and dimethylallyl diphosphate (DMAPP). Isoprenoids and their derivatives are categorized into groups based on the number of isoprene units: hemiterpenes (C5), monoterpenes (C10), sesquiterpenes (C15), diterpenes (C20), triterpenes (C30), tetraterpenes (C40), and polyterpenes (>C40)

All bacteria use molecules called polyprenyl phosphates (Pol-P), a long chain isoprenoid, as glycosyl carriers in the biosynthesis of their cell wall. Both *Escherichia coli* (*E. coli*) and *Mycobacterium tuberculosis* (Mtb) utilize isoprenoid glycosyl carriers for cell wall and membrane biosynthesis but their carriers differ slightly. *E. coli* utilizes undecaprenyl diphosphate (UPP), composed of 11 stereospecific isoprene units, while Mtb utilizes decaprenyl diphosphate

TABLE 3

| Name | Description | Modifiers |
|---|---|---|
| Negative control | IPP/DMAPP no enz | Keep in water bath overnight |
| Positive control | 10 μM GGPP no enz | Keep in water bath for 30 minutes |
| Rv1086 control | IPP/DMAPP + Rv1086 | Keep in water bath for 30 minutes |
| Rv0562/Rv3383c control | IPP/EEFPP + Rv0562/3383c | Keep in water bath for 30 minutes |
| Rv0562/Rv3383c + ZEFPP | IPP/ZEFPP + Rv0562/3383c | Keep in water bath for 30 minutes |
| Rv0562/Rv3383c + ZEFPP | IPP/ZEFPP + Rv0562/3383c | Keep in water bath overnight |
| Experiment 1 | IPP/DMAPP + Rv1086 + Rv0562/3383c | 20 μL clarified lysate, keep in water bath for 30 minutes |
| Experiment 2 | IPP/DMAPP + Rv1086 + Rv0562/3383c | 300 μg Rv1086 and either GGPP synthase, keep in water bath for 30 minutes |
| Experiment 3 | IPP/DMAPP + Rv1086 + Rv0562/3383c | 100 μL Rv1086 and either GGPP synthase, keep in water bath for 30 minutes |
| Experiment 4 | IPP/DMAPP + Rv1086 + Rv0562/3383c | 100 μL Rv1086 and either GGPP synthase, keep in water bath overnight |
| Experiment 5 | IPP/DMAPP + Rv1086, wait then add Rv0562/3383c | 300 μg each enzyme; allow Rv1086, IPP/DMAPP to incubate for ten minutes then add GGPP synthase |
| Experiment 6 | Rv1086 + Rv0562/3383c, wait then add IPP/DMAPP | 100 μL each enzyme; allow Rv1086 and either GGPP synthase to incubate for ten minutes then add IPP/DMAPP |

Example 4

Terpenoids, a large class of natural products, are commonly used by organisms in the kingdom Bacteria for cell wall and membrane biosynthesis and electron transportation. *Mycobacterium tuberculosis* (Mtb) utilizes terpenoid glycosyl carriers to assemble extracellular matrices. Mtb uses three main enzymes to produce Z8,E-decaprenyl diphosphate (Z8,E-DPP): two isoprene units are polymerized to produce E-geranyl diphosphate (Rv0989c), which is elongated by Z-FPP synthase (Rv1086) to produce Z,E-Farnesyl diphosphate (Z,E-FPP) which is elongated to Z,E-DPP by (DPP), composed of 10 stereospecific isoprene units. Three main enzymes are employed by Mtb to synthesize DPP: E-geranyl diphosphate (E-GPP) is formed by an isoprenyl synthase encoded by gene Rv0989 that polymerizes two isoprene units. This product is subsequently elongated by a cis prenyltransferase, Z-FPP synthase, encoded by Rv1086 to produce Z,E-Farnesyl diphosphate (Z,E-FPP). This product has been found to be the precursor of Z9,E-DPP, which is formed by decaprenyl diphosphate synthase(DPPS) encoded by gene Rv2361c that adds seven IPP units on the previous molecule, all in a cis conformation DPP is able to catalyze the addition of IPP to GPP, E,E-FPP, NPP, and E,E,E-GGPP (Kaur et al., 2004). One of the substrates, E,E,E-Geranylgeranyl diphosphate (E,E,E-GGPP), can be synthesized by Mtb's GGPP synthases encoded by Rv3383c and Rv0562. The enzyme encoded by Rv0562 can synthesize GGPP starting from different substrates as E,E-FPP, DMAPP, and GPP while the GGPP synthase encoded by Rv3383c can only synthesize its product starting from E,E-FPP.

The expression and purification of Rv0562 and Rv3383c confirmed that the size of the enzyme encoded by Rv0562 was about 35528 Da, while the one encoded by Rv3383c was about 36432 Da.

Large quantities of (E,Z,E)-GGPP and derivatives thereof are produced and assessed for selectivity, toxicity, and mechanism of action (MOA). Specifically, the compounds are tested against 21 prokaryotes and 3 eukaryotes (fungi of varying genus) to determine if there is a specificity to the bactericidal effect. In addition, the mechanism of action of this compound may be deduced by assaying it against the most likely target, the cell wall glycocarrier, E. coli undecaprenyl diphosphate synthase (UPPS), using a quick and easy colorimetric assay.

Example 5

Antibiotic scaffolds are one of medicine's greatest needs as bacteria continue their race to evolve antibiotic resistance. Recently, a greater understanding of the human microbiome has illuminated the necessity for selective antibiotic compounds to reduce harm to the natural flora of the antibiotic recipient. A classic source of new antibiotics has been microbes themselves. Typically, discovery of these molecules has been dependent on secretion of the compounds into the microbial environment, however, molecular biology has now made it possible to reconstitute biosynthetic pathways in heterologous hosts.

Classically, novel antibiotic compounds have been discovered from bacteria and fungi. Typically, such compounds are excreted by the microorganisms in a form of 'chemical warfare' between microbes (Lucas et al., 2009). However, due to small discrepancies in metabolism, compounds that are synthesized in one bacterium can act as inhibitors for metabolism in another bacterium. As disclosed herein a compound was produced by combining two enzymes from *Mycobacterium tuberculosis* (Mtb) and demonstrates toxicity in *Escherichia coli* (*E. coli*). Specifically, in an effort to understand the metabolism of a specific class of compounds referred to as isoprenoids, multiple combinations of genes encoding isoprenoid synthases from Mtb were expressed in the host *E. coli*. Of the dozens of individual and combinatorial genes tested, only two combinations resulted in significant cell death within the host. It was hypothesized that the combination of enzymes generated a single, unique compound unique to *E. coli* metabolism, (E,Z,E)-GGPP, which was subsequently produced in vitro.

Large Scale Production of (E,Z,E)-GGPP and Derivatives for Antibiotic and Functional Studies (E,Z,E)-GGPP can be produced biosynthetically using purified recombinant enzymes, resulting in an aqueous mix of enzymes, unreacted substrates, product, and salts. Purification of the product is most easily performed by dephosphorylation to the primary alcohol ((E,Z,E)-geranylgeraniol, or "GGOH") and separation to an organic solvent. GGOH can be tested for bioactivity. Further derivatization may generate a compound that is membrane permeable, e.g., see Davidson et al., 2006, Keller et al., 1993: Shul et al., 2006). Three derivatizations are specifically envisioned: first, GGOH is converted into a halide (e.g., chloro-geranylgeranene, or "GGCl"), which provides a starting place for further modifications to the purified pyrophosphate (GGPP) and the purified bisphosphonate (e.g., GGPmP). GGPP is important for mechanism of action studies, and GGPmP takes advantage of previously known bioactivity of bisphosphonates, which are a class of compounds already approved for use in humans to treat a variety of disorders (Hinshaw et al., 2016) and they have demonstrated bioavailability and permeability when assayed in microbes (Malwal et al., 2019). Derivatizing to a bisphosphonate provides the combination of a hydrocarbon skeleton with a previously successful drug class.

Assessment of Toxicity Against Common Prokaryotic and Eukaryotic Organisms and Comparison to Compounds of Similar Biological Activity Data indicates E,Z,E-GGPP may be selectively toxic to specific bacteria. Antibiotic selectivity is becoming more important when considering the role of the human microbiota and the effect antibiotic drugs would have on these microbes. Toxicity is assessed against a diverse array of microbes to ascertain selectivity. Specifically, 24 different genus of bacteria and three fungi are exposed to GGOH, GGPP, and GGPmP. Toxicity is first ascertained via an Ames test and then quantified via cell death assays.

Assessment of the Mechanism of Action of (E,Z,E)-GGPP and its Derivatives

Due to the differences in isoprenoid metabolism in Mtb and *E. coli*, the mechanism of action (MOA) of (E,Z,E)-GGPP is likely competitive inhibition of the *E. coli* glycocarrier undecaprenyl diphosphate synthase (UPPS).

Example 6

The disclosure provides a compound having the structure (I):

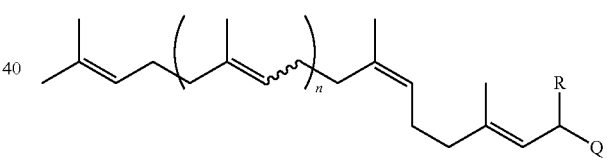

wherein
n is an integer between 1 and 20 so as to represent a number of repeating groups each instance of which independently has a stereochemistry of E or Z;
Q is a phosphate, —OX, halide;
X is hydrogen, an ester, or a biomolecule; and
R is H, or when Q is a phosphate, then R is H or a dimer group so as to provide a bisphosphonate dimer;
or a salt thereof.

In one embodiment, the phosphate is a monophosphate, diphosphate, or triphosphate, or a salt thereof. In one embodiment, Q is diphosphate, or a salt thereof. In one embodiment, the compound has the structure:

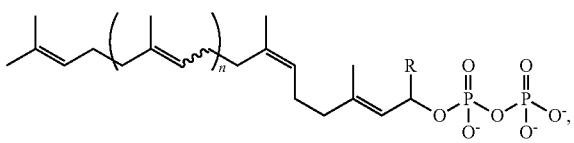

or a salt thereof.

In one embodiment, the compound has the structure:

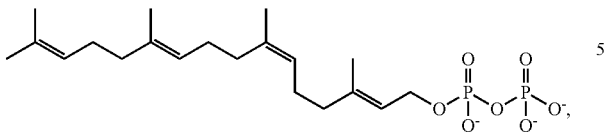

or a salt thereof. In one embodiment, Q is a phosphate and R is a dimer group so as to provide a bisphosphonate dimer, or a salt thereof. In one embodiment, the compound has the structure:

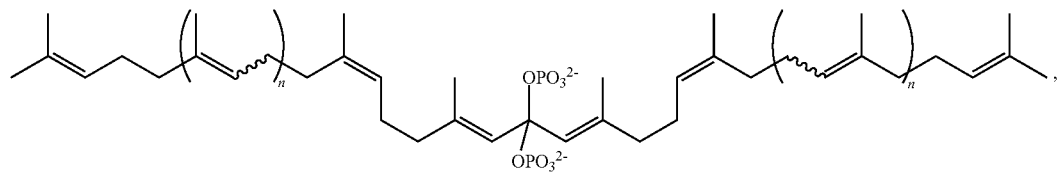

or a salt thereof.

In one embodiment, the compound has the structure:

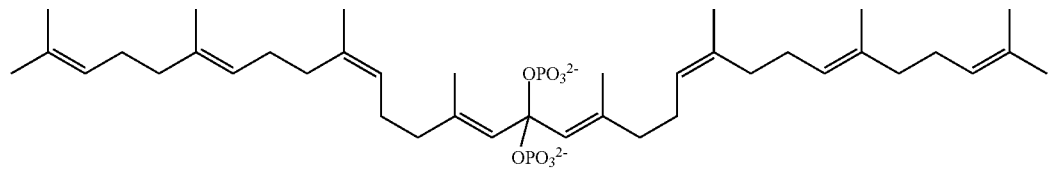

or a salt thereof. In one embodiment, the biomolecule is a protein linked via a cysteine residue. In one embodiment, the compound has the structure:

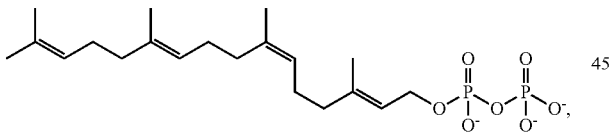

or salt thereof.

In one embodiment, the compound is in the form of a sodium, potassium, magnesium, calcium, or ammonium salt.

The disclosure further provides a compound having the structure (III):

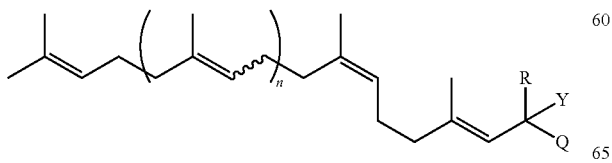

wherein
n is 1 or an integer from 2 to 20 so as to represent a number of repeating groups each instance of which independently has a stereochemistry of E or Z;
Q is a phosphate, a phosphonate, X, OH, —OX, halide, alkylsulfonyl, or arylsulfonyl;
Y is H or a phosphonate;
X is a phosphonate, an ester, or a biomolecule; and
R is H, alkyl, or a dimer group;
or a salt thereof. In one embodiment, when Q is a phosphonate and Y is a phosphonate, then R is an alkyl or a dimer group so as to provide a bisphosphonate, or a salt thereof. In one embodiment, when Q is other than phosphonate, then Y is H and R is H. In one embodiment, the structure is: E,Z,E-Geranylgeranyl methyl bisphosphonate, or a salt thereof; E,Z,E-Geranylgeranyl bisphosphonate, or a salt thereof; E,Z,E-Geranylgeraniol; E,Z,E-Geranylgeranyl chloride; E,Z,E-Geranylgeranyl tosylate; or E,Z,E-Geranylgeranyl pyrophosphate. In one embodiment, the structure is:

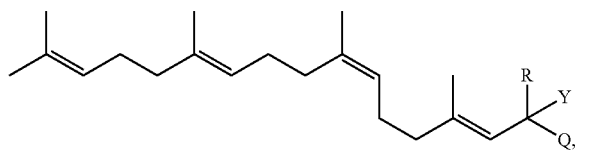

or a salt thereof.

In one embodiment, the phosphate is a monophosphate, diphosphate, or triphosphate, or a salt thereof. In one embodiment, Q is diphosphate, or a salt thereof. In one embodiment, the structure is:

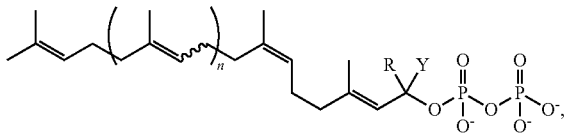

or a salt thereof.

In one embodiment, the structure is:

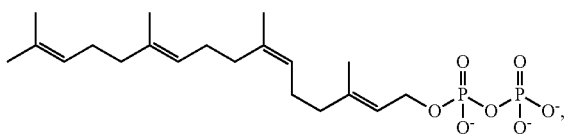

or a salt thereof.

In one embodiment, Q is a phosphate and R is a dimer group so as to provide a bisphosphonate dimer, or a salt thereof. In one embodiment, the structure is:

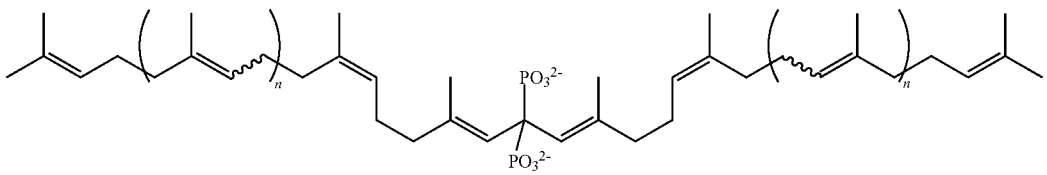

or a salt thereof.

In one embodiment, the structure is:

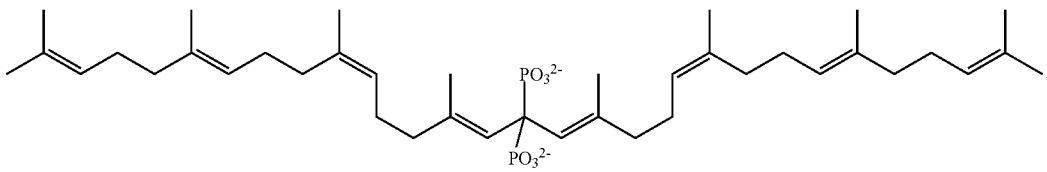

or a salt thereof.

In one embodiment, the biomolecule is a protein linked via a cysteine residue. In one embodiment, the structure is:

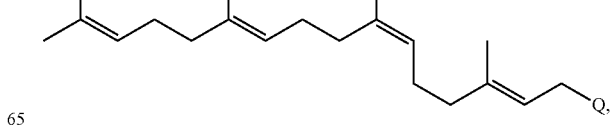

or salt thereof.

In one embodiment, the compound in a fully or partially protonated form, in a neutral form, or in the form of a sodium, potassium, magnesium, calcium, or ammonium salt. Also provided is a prodrug, derivative, or biosynthetic product, which is derived from the compound of structure (III). In one embodiment, the prodrug, derivative, or biosynthetic product, comprising a diterpene having E,Z,E stereochemistry. In one embodiment, the prodrug, derivative, or biosynthetic product, which is a prenylated with E,Z,E-GG.

Further provided is a prodrug, derivative, or biosynthetic product, which is derived from the compound having the structure (I), (II) or (III), or a composition comprising the compound having the structure (I), (II) or (III). In one embodiment, a composition having the compound having the structure (I), (II) or (III), contains less than 1 wt %4 of E,E,E-GGPP. In one embodiment, a composition having the compound having the structure (I) is substantially free of E,E,E-GGPP. In one embodiment, a composition having the compound having the structure (I), (II) or (III), is substantially free of naturally occurring stereoisomers of GGPP. In one embodiment, a composition having the compound having the structure (I), (II) or (III), is substantially free of naturally occurring stereoisomers. In one embodiment, a composition having the compound having the structure (I), (II) or (III), further comprises a pharmaceutically acceptable carrier. In one embodiment, a composition having the compound having the structure (I), (II) or (III), is formulated for topical administration.

REFERENCES

Czarny, T. L. and E. D. Brown, *A Small-Molecule Screening Platform for the Discovery of Inhibitors of Undecaprenyl Diphosphate Synthase*. ACS Infect Dis, 2016. 2(7): p. 489-99.

Davisson, V. J. W., A. B., et al., *Phosphorylation of Isoprenoid Alcohols*. J. Org. Chem., 1986. 51: p. 4678-4779.

Hinshaw, W. B. and A. F. DeLong, *An Evaluative History of Bisphosphonate Drugs: Dual Physiologic Effects of Pyrophosphate as Inspiration for a Novel Pharmaceutical Class*. J Osteoporos, 2016. 2016: p. 1426279.

Kaur, Devinder., et al. "Decaprenyl diphosphate synthesis in *Mycobacterium tuberculosis*." Journal of bacteriology vol. 186, 22 (2004): 7564-70. doi:10. 1128/JB.186.22.7564-7570.2004.

Keller, R. K. and R. Thompson, *Rapid synthesis of isoprenoid diphosphates and their isolation in one step using either thin layer or flash chromatography*. J Chromatogr, 1993. 645(1): p. 161-7.

Leon, A., et al., *Isoprenoid biosynthesis as a drug target: bisphosphonate inhibition of Escherichia coli K12 growth and synergistic effects of fosmidomycin*. J Med Chem, 2006. 49(25): p. 7331-41.

Liu, C. I., et al., *A cholesterol biosynthesis inhibitor blocks Staphylococcus aureus virulence*. Science, 2008. 319 (5868): p. 1391-4.

Lucas, J. M., et al., *Antibiotics as chemical warfare across multiple taxonomic domains and trophic levels in brown food webs*. Proc Biol Sci, 2019. 286(1911): p. 20191536.

Malwal, S. R., et al., *Discovery of Lipophilic Bisphosphonates That Target Bacterial Cell Wall and Quinone Biosynthesis*. J Med Chem, 2019. 62(5): p. 2564-2581.

Mann, Francis, Xu, Meimei & Davenport, Emily & Peters, Reuben. (2012). *Functional characterization and evolution of the isotuberculosinoloperon in Mycobacterium tuberculosis and related Mycobacteria*. Frontiers in microbiology. 3. 368. 10.3389/fmicb.2012.00368.

Poulos, L. M., Francis M., *Production of E,Z,E-GGPP: A potentially bactericidal non-natural product from Mycobacterium tuberculosis*. US Provisional Patent Application, 2020.

Schulbach, Mark C., et al. "Identification of a Short (C15) ChainZ-IsoprenylDiphosphate Synthase and a Homologous Long (C50) Chain Isoprenyl Diphosphate Synthase In *Mycobacterium Tuberculosis*." Journal of Biological Chemistry, vol. 275, no. 30, 2000, pp. 22876-22881.

Shull, L. W., et al., *Synthesis and biological activity of isoprenoid bisphosphonates*. Bioorg Med Chem, 2006. 14(12): p. 4130-6.

Wang, Y., et al., *Bacterial Cell Growth Inhibitors Targeting Undecaprenyl Diphosphate Synthase and Undecaprenyl Diphosphate Phosphatase*. ChemMedChem, 2016. 11(20): p. 2311-2319.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A compound having the structure (III):

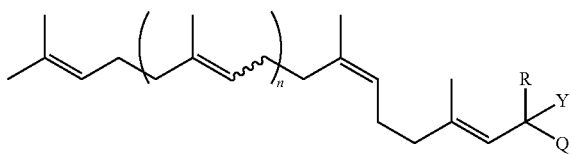

wherein n is 1 or an integer from 2 to 20 so as to represent a number of repeating groups each instance of which independently has a stereochemistry of E or Z;

Q is a phosphate, a phosphonate, X, OH, —OX, halide, alkylsulfonyl, or arylsulfonyl;

Y is H or a phosphonate;

X is a phosphonate, an ester, or a biomolecule; and

R is H, alkyl, or a dimer group;

or a salt thereof; and further comprising a pharmaceutically acceptable carrier.

2. The composition of claim 1 which is for topical administration.

3. An in vitro method to produce E,Z,E-GGPP, comprising: combining at least one isolated trans-isoprenyl diphosphate synthase having at least 90% amino acid sequence identity to SEQ ID NO: 2 or SEQ ID NO: 3, and at least two substrates therefore, or combining at least one isolated cis-isoprenyl diphosphate synthase having at least 90% amino acid sequence identity to SEQ ID NO: 1, at least one isolated trans-isoprenyl diphosphate synthase having at least 90% amino acid sequence identity to SEQ ID NO: 2 or SEQ ID NO: 3, and a substrate for the cis-isoprenyl diphosphate synthase, in an amount effective to produce E,Z,E-GGPP.

4. The compound of claim 1, wherein when Q is a phosphonate and Y is a phosphonate, then R is an alkyl or a dimer group so as to provide a bisphosphonate, or a salt thereof.

5. The compound of claim 1, wherein when Q is other than phosphonate, then Y is H and R is H.

6. The compound of claim 1, wherein structure is: E,Z,E-Geranylgeranyl methyl bisphosphonate or a salt thereof, E,Z,E-Geranylgeranyl bisphosphonate nor a salt thereof, E,Z,E-Geranylgeraniol, E,Z,E-Geranylgeranyl chloride, E,Z,E-Geranylgeranyl tosylate, or E,Z,E-Geranylgeranyl pyrophosphate.

7. The compound of claim 1, wherein the structure is:

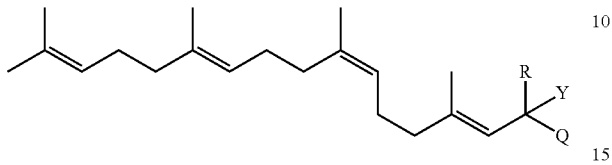

or a salt thereof.

8. The compound of claim 1, wherein the phosphate is a monophosphate, diphosphate, or triphosphate, or a salt thereof.

9. The compound of claim 1, wherein the structure is:

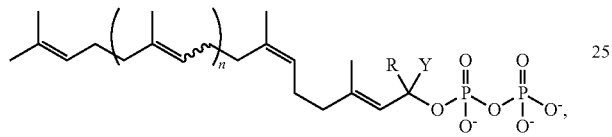

or a salt thereof.

* * * * *

SEQUENCE LISTING

```
<160> NUMBER OF SEQ ID NOS: 11

<210> SEQ ID NO 1
<211> LENGTH: 262
<212> TYPE: PRT
<213> ORGANISM: Artificial Sequence
<220> FEATURE:
<223> OTHER INFORMATION: A synthetic sequence

<400> SEQUENCE: 1

Met Glu Ile Ile Pro Pro Arg Leu Lys Glu Pro Leu Tyr Arg Leu Tyr
1               5                   10                  15

Glu Leu Arg Leu Arg Gln Gly Leu Ala Ala Ser Lys Ser Asp Leu Pro
            20                  25                  30

Arg His Ile Ala Val Leu Cys Asp Gly Asn Arg Arg Trp Ala Arg Ser
```

```
                35                  40                  45
Ala Gly Tyr Asp Asp Val Ser Tyr Gly Tyr Arg Met Gly Ala Ala Lys
             50                  55                  60
Ile Ala Glu Met Leu Arg Trp Cys His Glu Ala Gly Ile Glu Leu Ala
 65                  70                  75                  80
Thr Val Tyr Leu Leu Ser Thr Glu Asn Leu Gln Arg Asp Pro Asp Glu
                 85                  90                  95
Leu Ala Ala Leu Ile Glu Ile Thr Asp Val Val Glu Glu Ile Cys
            100                 105                 110
Ala Pro Ala Asn His Trp Ser Val Arg Thr Val Gly Asp Leu Gly Leu
            115                 120                 125
Ile Gly Glu Glu Pro Ala Arg Arg Leu Arg Gly Ala Val Glu Ser Thr
130                 135                 140
Pro Glu Val Ala Ser Phe His Val Asn Val Ala Val Gly Tyr Gly Gly
145                 150                 155                 160
Arg Arg Glu Ile Val Asp Ala Val Arg Ala Leu Leu Ser Lys Glu Leu
                165                 170                 175
Ala Asn Gly Ala Thr Ala Glu Glu Leu Val Asp Ala Val Thr Val Glu
            180                 185                 190
Gly Ile Ser Glu Asn Leu Tyr Thr Ser Gly Gln Pro Asp Pro Asp Leu
            195                 200                 205
Val Ile Arg Thr Ser Gly Glu Gln Arg Leu Ser Gly Phe Leu Leu Trp
210                 215                 220
Gln Ser Ala Tyr Ser Glu Met Trp Phe Thr Glu Ala His Trp Pro Ala
225                 230                 235                 240
Phe Arg His Val Asp Phe Leu Arg Ala Leu Arg Asp Tyr Ser Ala Arg
                245                 250                 255
His Arg Ser Tyr Gly Arg
            260

<210> SEQ ID NO 2
<211> LENGTH: 335
<212> TYPE: PRT
<213> ORGANISM: Artificial Sequence
<220> FEATURE:
<223> OTHER INFORMATION: A synthetic sequence

<400> SEQUENCE: 2

Met Arg Thr Pro Ala Thr Val Val Ala Gly Val Asp Leu Gly Asp Ala
 1               5                  10                  15
Val Phe Ala Ala Val Arg Ala Gly Val Ala Arg Val Glu Gln Leu
             20                  25                  30
Met Asp Thr Glu Leu Arg Gln Ala Asp Glu Val Met Ser Asp Ser Leu
            35                  40                  45
Leu His Leu Phe Asn Ala Gly Gly Lys Arg Phe Arg Pro Leu Phe Thr
 50                  55                  60
Val Leu Ser Ala Gln Ile Gly Pro Gln Pro Asp Ala Ala Ala Val Thr
 65                  70                  75                  80
Val Ala Gly Ala Val Ile Glu Met Ile His Leu Ala Thr Leu Tyr His
                 85                  90                  95
Asp Asp Val Met Asp Glu Ala Gln Val Arg Arg Gly Ala Pro Ser Ala
            100                 105                 110
Asn Ala Gln Trp Gly Asn Asn Val Ala Ile Leu Ala Gly Asp Tyr Leu
            115                 120                 125
Leu Ala Thr Ala Ser Arg Leu Val Ala Arg Leu Gly Pro Glu Ala Val
```

```
            130                 135                 140
Arg Ile Ile Ala Asp Thr Phe Ala Gln Leu Val Thr Gly Gln Met Arg
145                 150                 155                 160

Glu Thr Arg Gly Thr Ser Glu Asn Val Asp Ser Ile Glu Gln Tyr Leu
                165                 170                 175

Lys Val Val Gln Glu Lys Thr Gly Ser Leu Ile Gly Ala Ala Gly Arg
                180                 185                 190

Leu Gly Gly Met Phe Ser Gly Ala Thr Asp Glu Gln Val Glu Arg Leu
                195                 200                 205

Ser Arg Leu Gly Gly Val Val Gly Thr Ala Phe Gln Ile Ala Asp Asp
                210                 215                 220

Ile Ile Asp Ile Asp Ser Glu Ser Asp Glu Ser Gly Lys Leu Pro Gly
225                 230                 235                 240

Thr Asp Val Arg Glu Gly Val His Thr Leu Pro Met Leu Tyr Ala Leu
                245                 250                 255

Arg Glu Ser Gly Pro Asp Cys Ala Arg Leu Arg Ala Leu Leu Asn Gly
                260                 265                 270

Pro Val Asp Asp Ala Glu Val Arg Glu Ala Leu Thr Leu Leu Arg
                275                 280                 285

Ala Ser Pro Gly Met Ala Arg Ala Lys Asp Val Leu Ala Gln Tyr Ala
                290                 295                 300

Ala Gln Ala Arg His Glu Leu Ala Leu Leu Pro Asp Val Pro Gly Arg
305                 310                 315                 320

Arg Ala Leu Ala Ala Leu Val Asp Tyr Thr Val Ser Arg His Gly
                325                 330                 335

<210> SEQ ID NO 3
<211> LENGTH: 350
<212> TYPE: PRT
<213> ORGANISM: Artificial Sequence
<220> FEATURE:
<223> OTHER INFORMATION: A synthetic sequence

<400> SEQUENCE: 3

Met Gly Gly Val Leu Thr Leu Asp Ala Ala Phe Leu Gly Ser Val Pro
1               5                   10                  15

Ala Asp Leu Gly Lys Ala Leu Leu Glu Arg Ala Arg Ala Asp Cys Gly
                20                  25                  30

Pro Val Leu His Arg Ala Ile Glu Ser Met Arg Glu Pro Leu Ala Thr
                35                  40                  45

Met Ala Gly Tyr His Leu Gly Trp Trp Asn Ala Asp Arg Ser Thr Ala
                50                  55                  60

Ala Gly Ser Ser Gly Lys Tyr Phe Arg Ala Ala Leu Val Tyr Ala Ala
65                  70                  75                  80

Ala Ala Ala Cys Gly Gly Asp Val Gly Asp Ala Thr Pro Val Ser Ala
                85                  90                  95

Ala Val Glu Leu Val His Asn Phe Thr Leu Leu His Asp Asp Val Met
                100                 105                 110

Asp Gly Asp Ala Thr Arg Arg Gly Arg Pro Thr Val Trp Ser Val Trp
                115                 120                 125

Gly Val Gly Val Ala Ile Leu Leu Gly Asp Ala Leu His Ala Thr Ala
                130                 135                 140

Val Arg Ile Leu Thr Gly Leu Thr Asp Glu Cys Val Ala Val Arg Ala
145                 150                 155                 160

Ile Arg Arg Leu Gln Met Ser Cys Leu Asp Leu Cys Ile Gly Gln Phe
```

```
                    165                 170                 175
Glu Asp Cys Leu Leu Glu Gly Gln Pro Glu Val Thr Val Asp Asp Tyr
            180                 185                 190
Leu Arg Met Ala Ala Gly Lys Thr Ala Ala Leu Thr Gly Cys Cys Cys
            195                 200                 205
Ala Leu Gly Ala Leu Val Ala Asn Ala Asp Ala Thr Ile Ala Ala
        210                 215                 220
Leu Glu Arg Phe Gly His Glu Leu Gly Leu Ala Phe Gln Cys Val Asp
225                 230                 235                 240
Asp Leu Ile Gly Ile Trp Gly Asp Pro Gly Val Thr Gly Lys Pro Val
                245                 250                 255
Gly Asn Asp Leu Ala Arg Arg Lys Ala Thr Leu Pro Val Val Ala Ala
            260                 265                 270
Leu Asn Ser Arg Ser Glu Ala Ala Thr Glu Leu Ala Ala Leu Tyr Gln
            275                 280                 285
Ala Pro Ala Ala Met Thr Ala Ser Asp Val Glu Arg Ala Thr Ala Leu
        290                 295                 300
Val Lys Val Ala Gly Gly His Val Ala Gln Arg Cys Ala Asp Glu
305                 310                 315                 320
Arg Ile Gln Ala Ala Ile Ala Ala Leu Pro Asp Ala Val Arg Ser Pro
                325                 330                 335
Asp Leu Ile Ala Leu Ser Gln Leu Ile Cys Arg Arg Glu Cys
            340                 345                 350
```

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

```
<211> LENGTH: 262
<212> TYPE: PRT
<213> ORGANISM: Artificial Sequence
<220> FEATURE:
<223> OTHER INFORMATION: A synthetic sequence

<400> SEQUENCE: 10

Val Glu Ile Ile Pro Pro Arg Leu Lys Glu Pro Leu Tyr Arg Leu Tyr
1               5                   10                  15

Glu Leu Arg Leu Arg Gln Gly Leu Ala Ala Ser Lys Ser Asp Leu Pro
            20                  25                  30

Arg His Ile Ala Val Leu Cys Asp Gly Asn Arg Arg Trp Ala Arg Ser
        35                  40                  45

Ala Gly Tyr Asp Asp Val Ser Tyr Gly Tyr Arg Met Gly Ala Ala Lys
    50                  55                  60

Ile Ala Glu Met Leu Arg Trp Cys His Glu Ala Gly Ile Glu Leu Ala
65                  70                  75                  80

Thr Val Tyr Leu Leu Ser Thr Glu Asn Leu Gln Arg Asp Pro Asp Glu
                85                  90                  95

Leu Ala Ala Leu Ile Glu Ile Thr Asp Val Val Glu Glu Ile Cys
            100                 105                 110

Ala Pro Ala Asn His Trp Ser Val Arg Thr Val Gly Asp Leu Gly Leu
        115                 120                 125

Ile Gly Glu Glu Pro Ala Arg Arg Leu Arg Gly Ala Val Glu Ser Thr
    130                 135                 140

Pro Glu Val Ala Ser Phe His Val Asn Val Ala Val Gly Tyr Gly Gly
145                 150                 155                 160

Arg Arg Glu Ile Val Asp Ala Val Arg Ala Leu Leu Ser Lys Glu Leu
                165                 170                 175

Ala Asn Gly Ala Thr Ala Glu Glu Leu Val Asp Ala Val Thr Val Glu
            180                 185                 190

Gly Ile Ser Glu Asn Leu Tyr Thr Ser Gly Gln Pro Asp Pro Asp Leu
        195                 200                 205

Val Ile Arg Thr Ser Gly Glu Gln Arg Leu Ser Gly Phe Leu Leu Trp
    210                 215                 220

Gln Ser Ala Tyr Ser Glu Met Trp Phe Thr Glu Ala His Trp Pro Ala
225                 230                 235                 240

Phe Arg His Val Asp Phe Leu Arg Ala Leu Arg Asp Tyr Ser Ala Arg
                245                 250                 255

His Arg Ser Tyr Gly Arg
            260

<210> SEQ ID NO 11
<211> LENGTH: 335
<212> TYPE: PRT
<213> ORGANISM: Artificial Sequence
<220> FEATURE:
<223> OTHER INFORMATION: A synthetic sequence

<400> SEQUENCE: 11

Val Arg Thr Pro Ala Thr Val Val Ala Gly Val Asp Leu Gly Asp Ala
1               5                   10                  15

Val Phe Ala Ala Ala Val Arg Ala Gly Val Ala Arg Val Glu Gln Leu
            20                  25                  30

Met Asp Thr Glu Leu Arg Gln Ala Asp Glu Val Met Ser Asp Ser Leu
        35                  40                  45

Leu His Leu Phe Asn Ala Gly Gly Lys Arg Phe Arg Pro Leu Phe Thr
```

```
                50                  55                  60
Val Leu Ser Ala Gln Ile Gly Pro Gln Pro Asp Ala Ala Val Thr
 65                  70                  75                  80

Val Ala Gly Ala Val Ile Glu Met Ile His Leu Ala Thr Leu Tyr His
                     85                  90                  95

Asp Asp Val Met Asp Glu Ala Gln Val Arg Arg Gly Ala Pro Ser Ala
                    100                 105                 110

Asn Ala Gln Trp Gly Asn Asn Val Ala Ile Leu Ala Gly Asp Tyr Leu
                115                 120                 125

Leu Ala Thr Ala Ser Arg Leu Val Ala Arg Leu Gly Pro Glu Ala Val
            130                 135                 140

Arg Ile Ile Ala Asp Thr Phe Ala Gln Leu Val Thr Gly Gln Met Arg
145                 150                 155                 160

Glu Thr Arg Gly Thr Ser Glu Asn Val Asp Ser Ile Glu Gln Tyr Leu
                165                 170                 175

Lys Val Val Gln Glu Lys Thr Gly Ser Leu Ile Gly Ala Ala Gly Arg
                180                 185                 190

Leu Gly Gly Met Phe Ser Gly Ala Thr Asp Glu Gln Val Glu Arg Leu
                195                 200                 205

Ser Arg Leu Gly Gly Val Val Gly Thr Ala Phe Gln Ile Ala Asp Asp
            210                 215                 220

Ile Ile Asp Ile Asp Ser Glu Ser Asp Glu Ser Gly Lys Leu Pro Gly
225                 230                 235                 240

Thr Asp Val Arg Glu Gly Val His Thr Leu Pro Met Leu Tyr Ala Leu
                245                 250                 255

Arg Glu Ser Gly Pro Asp Cys Ala Arg Leu Arg Ala Leu Leu Asn Gly
                260                 265                 270

Pro Val Asp Asp Asp Ala Glu Val Arg Glu Ala Leu Thr Leu Leu Arg
                275                 280                 285

Ala Ser Pro Gly Met Ala Arg Ala Lys Asp Val Leu Ala Gln Tyr Ala
            290                 295                 300

Ala Gln Ala Arg His Glu Leu Ala Leu Leu Pro Asp Val Pro Gly Arg
305                 310                 315                 320

Arg Ala Leu Ala Ala Leu Val Asp Tyr Thr Val Ser Arg His Gly
                325                 330                 335
```